United States Patent [19]
Richards et al.

[11] Patent Number: 5,427,929
[45] Date of Patent: Jun. 27, 1995

[54] METHOD FOR REDUCING CARRYOVER CONTAMINATION IN AN AMPLIFICATION PROCEDURE

[75] Inventors: Rodney M. Richards, Louisville; Theodore Jones, Lakewood; David L. Snitman; Gregory S. Brown, both of Boulder, all of Colo.

[73] Assignee: Amgen Inc., Thousand Oaks, Calif.

[21] Appl. No.: 57,192

[22] Filed: May 3, 1993

Related U.S. Application Data

[63] Continuation of Ser. No. 686,478, Apr. 19, 1991, which is a continuation-in-part of Ser. No. 517,631, May 1, 1990, abandoned.

[51] Int. Cl.$^6$ .......................... C12P 19/34; C12Q 1/68
[52] U.S. Cl. ....................................... 435/91.2; 435/6; 935/77; 935/78
[58] Field of Search ........................................ 435/91.2

[56] References Cited

U.S. PATENT DOCUMENTS

| | | | |
|---|---|---|---|
| 4,683,195 | 7/1987 | Mullis et al. | 435/6 |
| 4,876,187 | 10/1989 | Duck et al. | 436/501 |
| 5,035,996 | 7/1991 | Hartley | 435/6 |

FOREIGN PATENT DOCUMENTS

| | | | |
|---|---|---|---|
| 0320308 | 6/1989 | European Pat. Off. | 435/6 |
| 0401037A2 | 5/1990 | European Pat. Off. | |
| WO89/11548 | 11/1989 | WIPO | |
| WO91/06665 | 5/1991 | WIPO | |

OTHER PUBLICATIONS

Strom et al., Am. J. Hum. Gen. 45(4 Suppl) 1989, abstract 0869/A221, 40th Ann. Mtg. Soc. Hum. Gen., Baltimore, Nov. 11–15, 1989.
Syvänen et al., Nuc. Acids. Res. 16(23):11327–11338 (1988).
Vosberg, Hum. Gen. 83(1):1–15 (1989).
Wu et al., Genomics 4:560–569 (1989).
Longo et al., Gen. 93(1990) 125–128.
Orlandi et al., Proc. Natl. Acad. Sci. USA 86(1989), 3833–3837.
Wong et al., Nat. (1987), 330–384.
Kwok et al., J. Virol., (1987), 61 1690–1694 (1987).
Bos et al, Nat., (1987), 327, 293 (1987).
Mullis, K. and Faloona, F., Methods in Enzymology, 155, 335–350 (1987).
Ou et al, Sci., 239, 295–297 (1987).
Saiki et al, Sci., 230, 1350–1354 (1988).
Engelke et al, Proc. Natl. Acad. Sci. USA, 85, 544–548 (1988).
Almoguera et al., Cell, (1988), 53, 549–554 (1988).
Higuchi et al., Nat., (1987), 332, 543–546 (1987).
Li et al., Nat., (1988), 335, 414–417 (1988).
Higuchi et al., Nuc. Acid. Res., 16(15), 7351 (1988).
Erlich et al., Nat., 331, 461–462 (1988).
Farr et al., Proc. Natl. Acad. Sci., USA, 85, 1629–1633 (1988).
Marx J L, Sci., (1988), 240, 1408–1410 (1988).
Oste C, Bio. Tech., 6(2), 162–167 (1988).
Mole et al., Nuc. Acid. Res., 17, 3319 (1989).

Primary Examiner—Stephanie W. Zitomer
Attorney, Agent, or Firm—Julia E. Abers

[57] ABSTRACT

The present invention provides an efficient and economical method for reducing carryover contamination in an amplification procedure. The method of the present invention enables background caused by contaminant amplification product to be reduced or eliminated through the incorporation of at least one modification into the amplification product. The modified amplification product is readily distinguishable from the target sequence in a test sample. Prior to amplifying the target in a new test sample, the sample may be treated to selectively cleave the contaminant amplification product so that it cannot be amplified in the new sample.

21 Claims, 32 Drawing Sheets

XL = Cross-Linking Agent

RS = Restriction Site

ψRS = Pseudo Ristriction Site x, x' = Nucleotide Mismatches to Amplification Sequence RS = Restriction Site ψRS = Pseudo Restriction Site x, x' = Nucleotide Mismatches to Amplification Sequence RS = Restriction Site x, x' = Nucleotide Mismatches to Amplification Sequence RS = Restriction Site ψRS = Pseudo Restriction Site CS = Cleavage Site x, x' = Nucleotide Mismatches to Amplification Sequence RS = Restriction Enzyme ψRS = Pseudo Restriction Enzyme CS = Cleavaage Site x, x' = Nucleotide Mismatches to Amplification Sequence FIG. 10
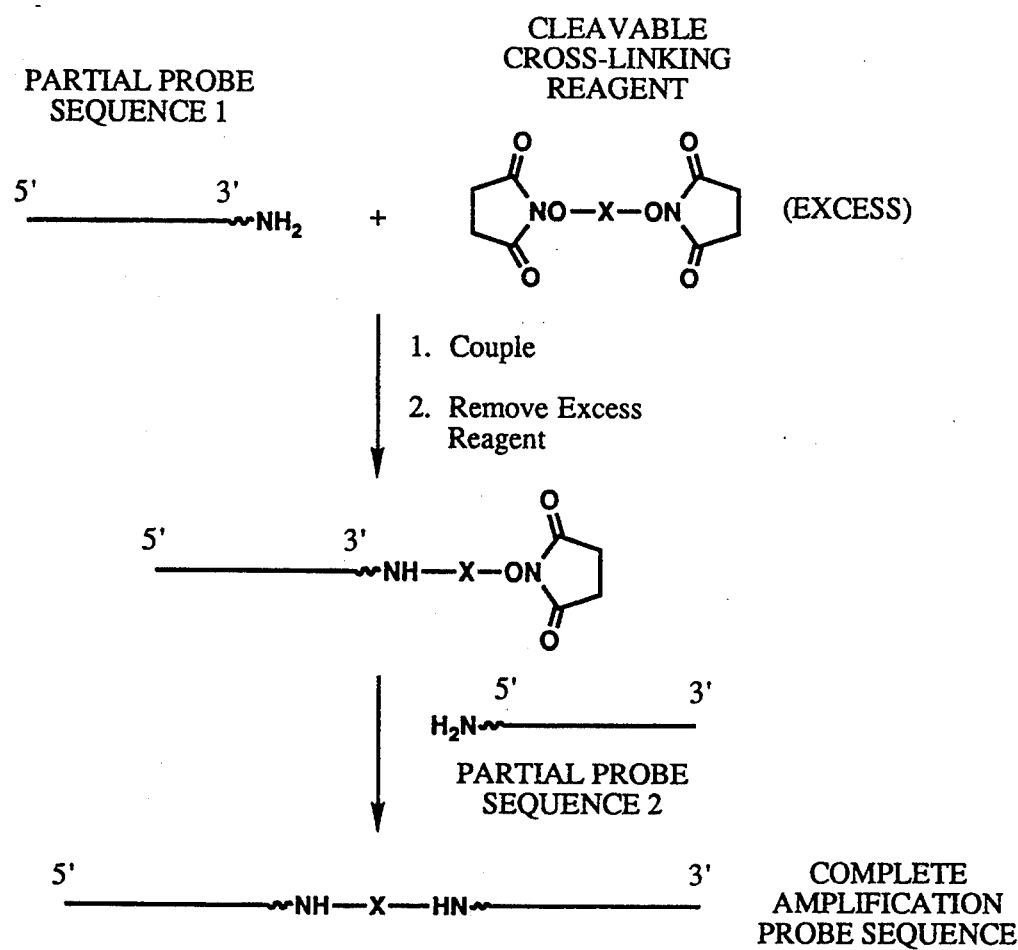
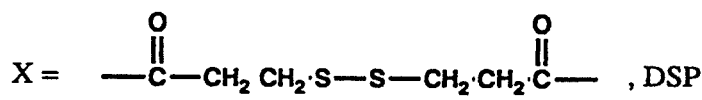, DSP
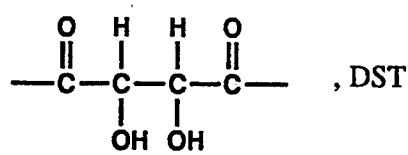, DST
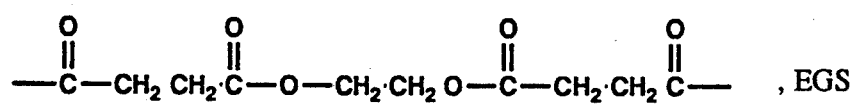, EGS

FIG. 11A
AMPLIFICATION SEQUENCE

AS₁
5'ATTGGATGAACAGCTAAGCTGTGACCAAGACATTCTCGGACTGCAATA3'
3'TAACCTACTTGTCGATTCGACACTGGTTCTGTAAGAGCCTGACGTTAT5'
AS₁'

FIG. 11B
AMPLIFICATION PROBES

AP₁
5'ATTGGATGAGCAGCTAA3'
3'TAACCTACTCGTCGATTp5'
AP₁' pAP₃
5'pATTCTCGGGCTGCAATA3'
3'TAAGAGCCCGACGTTAT5'
AP₃' pAP₂
5'pGCTGTGGCCAAGAC3'
3'CGACACCGGTTCTGp5'
pAP₂'

FIG. 11C
DETECTION PROBES

DP₁
5'ATTGGATGAGCAGCTAAGCTGTGG pDP₂
pCCAAGACATTCTCGG3'

FIG. 11D
AMPLIFICATION PRODUCT

AMP₁
5'ATTGGATGAGCAGCTAAGCTGTGGCCAAGACATTCTCGGCTGCAATA3'
3'TAACCTACTCGTCGATTCGACACCGGTTCTGTAAGAGCCCGACGTTAT5'
AMP₁'

FIG. 13A
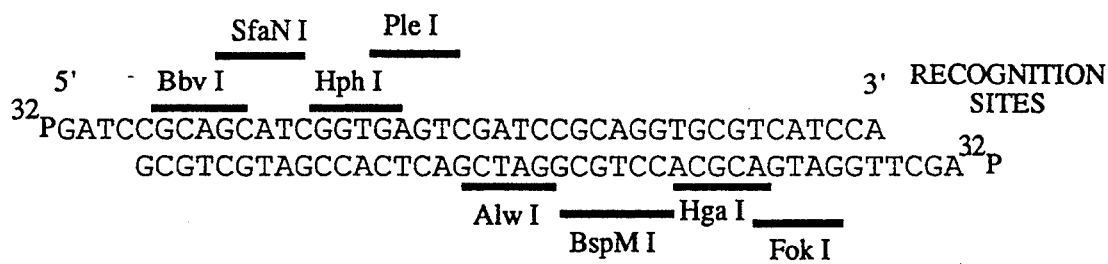
FIG. 13B
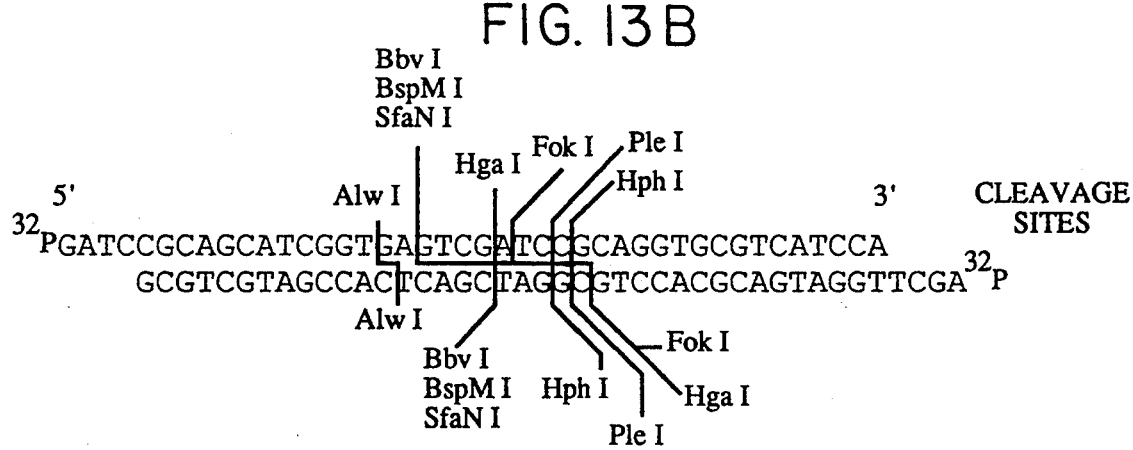
FIG. 13C
| RESTRICTION ENZYME | $^{32}P$ LABELED FRAGMENT SIZE (BASES) |
|---|---|
| Alw I | 16, 29 |
| Bbv I | 18, 24 |
| BspM I | 18, 24 |
| Fok I | 23, 19 |
| Ple I | 25, 20 |
| Hga I | 22, 19 |
| Hph I | 26, 19 |
| SfaN I | 18, 24 |

147 b.p.→

FIG. 23A
PAD$_5$
5' AAAACGTTACTCGACAGAGGAGAGCA 3'
FIG. 23B
AP$_{18}$
5' CGTTACTCGACAGA (rG) 3'
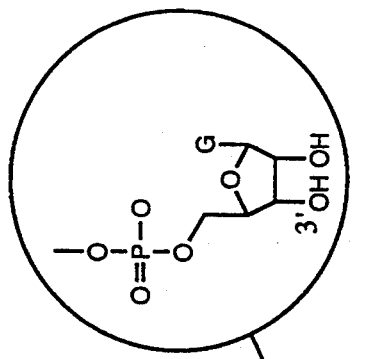
FIG. 23C
HIV TARGET
5' ∼∼∼CGTTACTCGACAGAGAGGAGCAAGAAATGGAGCCAAGTAGACTAGATCCAGTAGACCCTGGAAGCATCCAGGAAGTC∼∼∼ 3'
3' ∼∼∼GCAATGAGCTGTCTCCTCGTTCTTTACCTCGGTTCATCTGATCTAGGTCATCTGGGACCTTCGTAGGTCCTTCAG∼∼∼ 5'
FIG. 23D
(Ur) CGTAGGTCCTTCAG 5'
AP$_{21'}$
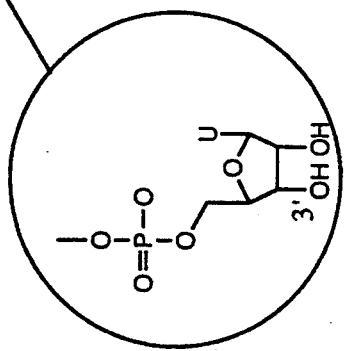

FIG. 28

```
       AP18                    pAP19                      pAP20
5'CGTTACTCGACAGA(rG)   pGAGAGCAAGAAATG(rG)   pAGCCAGTAGATCCT(rA) 3'

5'CGTTACTCGACAGAGGAGAGCAAGAAATGGAGCCAGTAGATCCTA 3'    TARGET
  3'GCAATGAGCTGTCTCCTCTCGTTCTTTACCTCGGTCATCTAGGAT 5'    SEQUENCE

3'GCAATGAGCTGTCTCp (Cr)TCTCGTTCTTTACCp (Ur)CGGTCATCTAGGATp 5'
      pAP18'                  pAP19'                    pAP20'
```

|LCR AMPLIFICATION|
↓

```
5'CGTTACTCGACAGA(rG) GAGAGCAAGAAATG(rG) AGCCAGTAGATCCT(rA) 3'
3'GCAATGAGCTGTCTC(Cr) TCTCGTTCTTTACC(Ur) CGGTCATCTAGGATp 5'
```
MODIFIED
AMPLIFICATION
PRODUCT p=phosphate group r=ribonucleotide

METHOD FOR REDUCING CARRYOVER CONTAMINATION IN AN AMPLIFICATION PROCEDURE

This is a continuation of copending application Ser. No. 07/686,478 filed on Apr. 19, 1991 which is a continuation-in-part of application Ser. No. 07/517,631 filed on May 1, 1990, now abandoned.

BACKGROUND

Diagnostic assays are routinely used to detect the presence and/or quantity of analytes in test samples taken from a patient or other subject. Typical analytes include antigens and antibodies, which are measured using immunodiagnostic techniques to identify certain disease states and various types of non-disease conditions, such as pregnancy. The achievement of high levels of sensitivity and specificity is important in most diagnostic assays. This is particularly true where the analytes of interest are present at relatively low concentrations. Various improvements which have enabled the attainment of higher levels of sensitivity in immunodiagnostic procedures have included the use of monoclonal antibodies in the assay configurations and the incorporation of methods for amplifying the signal used as a tag in these types of assays.

More recently, advances in the field of molecular biology have enabled the detection of specific nucleic acid sequences in test samples using a technique known as probe diagnostics. In probe diagnostics, a nucleic acid sequence is used to "probe" the sample by specifically binding to its complementary nucleic acid target analyte. This makes it possible to detect diseases at an early stage, because the nucleic acid genetic material often appears in a test sample months, or even years, before sufficient time has elapsed for the nucleic acid target to be transcribed into an antigen. This is particularly true in certain types of sexually transmitted diseases, such as infection by the human immunodeficiency virus. Ranki et al, *The Lancet*, 85(59) 589-593 (1987). In addition to the detection of various diseases and genetic disorders, the ability of probe diagnostics to identify the presence of specific genes can also be used to obtain other pertinent genetic information, such as the presence of genes coding for antigens responsible for graft rejection, as well as genetic information used in cancer and oncogene testing and in forensic medicine.

At its full potential, probe diagnostics are theoretically capable of detecting as little as one molecule in a test sample. One of the major obstacles to achieving the full potential of probe diagnostics is the inherent difficulty which is encountered in detecting the extremely minute quantities of target sequences often present in test samples. As a consequence, recent efforts to improve the sensitivity of probe diagnostics have centered around methods for amplifying the target nucleic acid sequence. Amplification of the target sequence may be accomplished in any one of a number of ways involving the repetitive reproduction or replication of the given DNA or RNA target nucleic acid sequence, resulting in linear or exponential amplification, depending upon the particular method used.

Early methods which were used routinely for production of multiple copies of nucleic acid sequences involved cloning the target nucleic acid sequence into an appropriate host cell system. These methods employ traditional cloning techniques wherein the desired nucleic acid is inserted into an appropriate vector which is subsequently used to transform the host. When the host is grown in culture, the vector is replicated, producing additional copies of the desired nucleic acid sequence. The target nucleic acid sequence which is inserted into the vector can be either naturally occurring or synthesized. In other words, the desired target nucleic acid sequence can be synthesized in vitro and then inserted into a vector which is amplified by growth, as disclosed in U.S. Pat. No. 4,293,652.

U.S. Pat. Nos. 4,683,195 and 4,683,202 disclose an automatable method, commonly referred to as polymerase chain reaction (PCR), for amplifying the amount of target nucleic acid sequence in a test sample. PCR amplification utilizes two oligonucleotide primers which are complementary to the ends of different portions on opposite strands of a section of the target sequence. Following hybridization of these primers to the target, extension products complementary to the target sequence are formed in the presence of DNA polymerase and an excess of nucleoside triphosphates. The primers are oriented so that DNA synthesis by the polymerase proceeds across and through the region between the primers. The hybridized extension product is then denatured from the target and the cycle repeated, with extension product also acting as template for the formation of additional extension product in subsequent cycles of amplification. Cycling continues until a sufficient quantity of the target nucleic acid sequence is produced to result in measurable signal in the assay of choice. Each successive cycle theoretically doubles the amount of nucleic acid synthesized in the previous cycle, resulting in exponential accumulation of amplified product.

International Publication No. WO 89/12696 discloses a different type of automatable amplification procedure. In this type of amplification procedure, presynthesized pairs of amplification probes hybridize contiguously to a section of the target sequence. The contiguous ends are then ligated to form the complementary amplification product. Following ligation, the completed amplification product is separated from the target by heat denaturation. The process is then repeated, with both the target and resulting amplification product acting as a template for the probes in subsequent cycles, until a sufficient quantity of the target nucleic acid sequence is produced to result in measurable signal in the selected assay. As with PCR, each successive cycle theoretically doubles the amount of nucleic acid from a previous cycle. Amplification methods employing presynthesized probes have generally been referred to as ligase chain reaction (LCR), although ligation of the probes can be achieved by means other than the action of a ligase, such as, for example, a chemical or photochemical ligation.

Although nucleic acid amplification methods have revolutionized probe diagnostics by enabling the detection of extremely small quantities of nucleic acid sequences in test samples, they have also created their own problem in the routine diagnostic setting, namely, one of false positives due to carryover contamination. The repeated amplification of a nucleic acid analyte to many millions or billions of times its normal concentration in a test sample raises the possibility of carryover contamination of new samples from the samples containing amplified target. This, in turn, can create artificially high signals in subsequent test samples, including false positives where negative samples are contaminated.

Carryover contamination may occur as the result of mechanical carryover from sample to sample or as the result of airborne contamination. Airborne contamination is unavoidable where reaction vessels containing amplified test sample are opened for any reason, such as for the addition of reagents or for sampling of the amplified analyte for detection. This act alone can aspirate millions of molecules of amplification product into the air, contaminating a normal laboratory work area with hundreds of molecules per cubic inch. Thus far, it has been impossible to completely guard against the contamination of other specimens through contact with these airborne copies, regardless of the degree of care exercised by the operator(s).

The following techniques for dealing with the contamination problems created by amplification of target sequences, although suggested for use in a PCR type of amplification procedure, would be generally applicable to other types of amplification procedures: (1) physical separation (such as separate rooms) of pre-amplification and post-amplification samples; (2) separate storage and aliquotting of reagents; (3) the use of positive displacement pipettes; (4) meticulous laboratory technique; and, (5) cautious selection of controls. *Amplifications—A forum for PCR Users,* 2, 4 (1989). These measures, however, are not only costly, but assume the most ideal of conditions. Furthermore, even if these expensive techniques are practiced fastidiously, precautions such as these cannot completely eliminate the contamination problem. There remain inherent difficulties from laboratory workers who invariably carry contamination on their bodies and clothes and from the circulation of contaminated air from room to room through air vents. Kitchin, *Nature,* 344, 201 (1990).

Treatment of reagents with ultraviolet light has been suggested for the control of contaminant amplification product in a PCR type of amplification procedure. This suggestion is based on the known ability of ultraviolet light to destroy the integrity of DNA. Although the mechanism for this action is unknown, it has been demonstrated that PCR-based contaminant amplification product can be destroyed in buffers as well as in primer, dNTP, and Taq polymerase preparations by irradiation with ultraviolet light. Sarkar et al, *Nature,* 343, 27 (1990). Although the single-stranded PCR primers are apparently able to survive this treatment, double-stranded pairs of LCR probes are likely to be more sensitive to the irradiation treatment, and may be destroyed. Furthermore, irradiation with ultraviolet light cannot be used directly on unassayed test samples, because this would result in the destruction of double-stranded target molecules by the irradiation treatment.

It is an objective of the present invention to provide a cost effective method for significantly reducing the carryover contamination encountered when using amplification procedures in diagnostic probe assays. It is a further objective of the present invention to provide a contamination reduction method which is simple to perform and which is adaptable to a number of different types of amplification procedures.

SUMMARY OF THE INVENTION

The present invention provides an efficient and economical method for reducing amplification product contamination in an amplification procedure. The method of the present invention is carried out by modifying the amplification product such that the modified amplification product is distinguishable from the target sequence. Prior to amplifying the target nucleic acid in a new test sample, the new sample may be treated in an appropriate manner to selectively remove, destroy, or otherwise render the modified contaminant amplification product nonviable so that it cannot be amplified in subsequent amplification procedures. Treatment in this way reduces carryover contamination, and the false positives caused by this type of contamination, without affecting levels of the naturally occurring target sequence.

BRIEF DESCRIPTION OF THE DRAWINGS

FIG. 10 shows the preparation of oligonucleotide amplification probes or primers incorporating a chemically cleavable site.

FIG. 11 shows the amplification sequence, amplification probes, resulting amplification product, and detection probes from Examples 1 and 2.

FIG. 13 shows the polysite DNA used in Example 3 to evaluate remote cutting restriction enzymes.

FIG. 23 is a diagram showing a 75 base pair HIV amplification sequence, two ribonucleotide modified PCR amplification primers, and a detection primer used in Example 6.

FIG. 28 is a diagram showing a 45 base pair HIV amplification sequence and the corresponding ribonucleotide modified amplification probes used to generate ribonucleotide modified LCR-derived amplification product in Example 7.

DETAILED DESCRIPTION OF THE INVENTION

Figure 1:
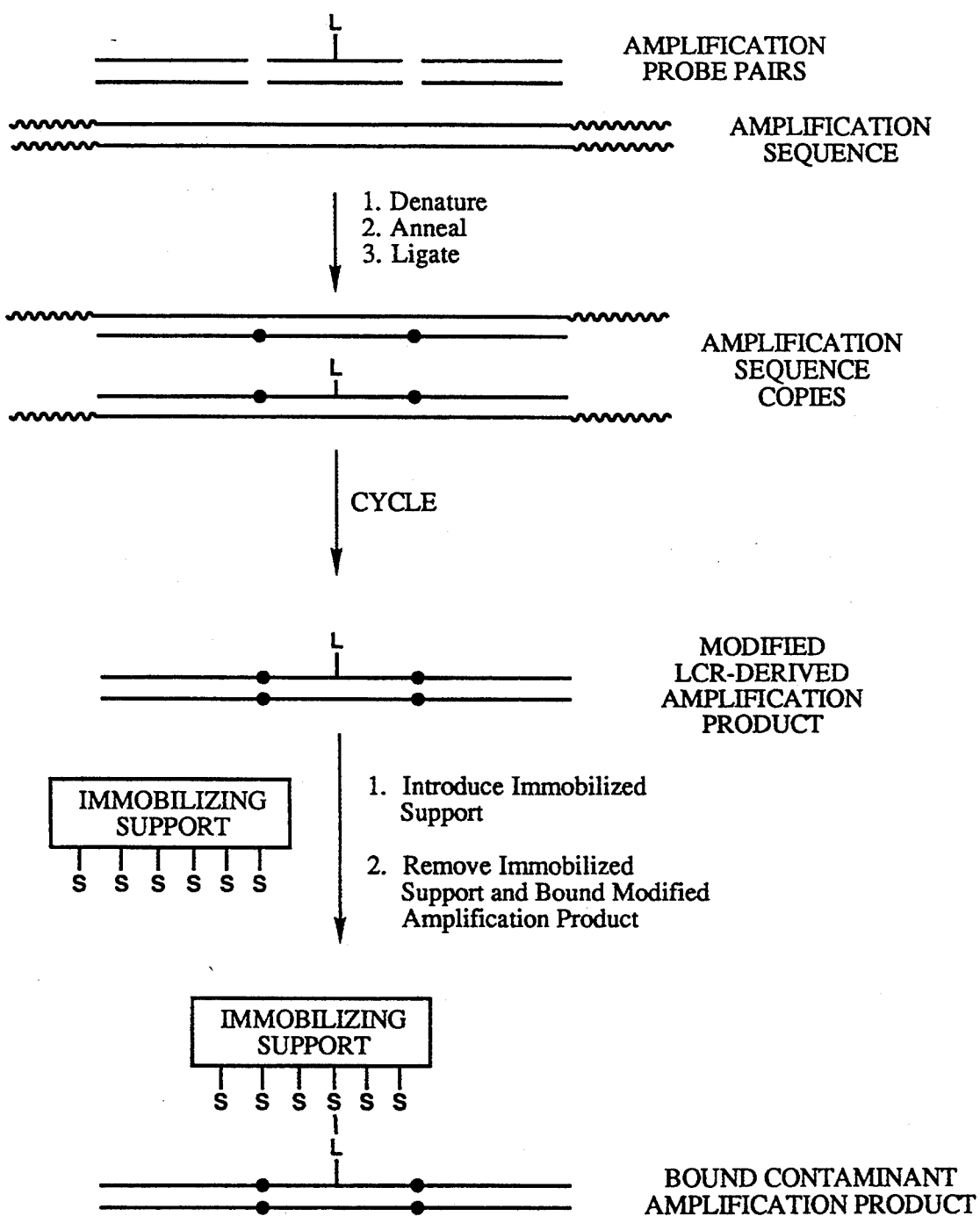
FIG. 1 is a diagram showing ligand modification of an LCR-derived amplification product and subsequent removal of the modified amplification product with immobilized specific binding partner.

The present invention enables background caused by contaminant amplification product to be reduced or eliminated through the incorporation of at least one modification into the amplification product. The modified amplification product is readily distinguishable from the target sequence in a test sample, and may be selectively eliminated.

In order to more clearly understand the invention, it will be useful to set forth the definitions of certain terms that will be used herein:

Amplification means increasing the number of copies of a nucleic acid sequence in a test sample. The copies which are generated during Amplification may be exact copies or complementary copies. In addition, the copies may be modified by a means for controlling contamination. Amplification may proceed in a linear manner or in an exponential manner; i.e., at a rate greater than linear Amplification.

Nucleic Acid Sequence is a deoxyribonucleotide or a ribonucleotide which may be modified with respect to: (1) the phosphate backbone; (2) the nucleosides; and/or, (3) the sugar moiety of the oligonucleotide. Nucleic ACid Sequences can contain labels or other attached moieties and can be interrupted by the presence of still other moieties, as long as hybridization can occur.

Target Sequence is the nucleotide sequence being sought in a particular assay.

Amplification Sequence is a designated length of the target sequence which initially acts as template sequence in an amplification procedure. The Amplification Sequence may comprise the entire length of the target sequence or a representative portion thereof.

Template Sequence is the nucleic acid sequence upon which amplification product is formed. In the first cycle of amplification, the amplification sequence acts as the Template Sequence. In subsequent cycles of amplification, amplification product also serves as a Template Sequence.

Amplification Probe is a nucleic acid sequence which is either: (1) complementary to a portion of a single strand of a double-stranded amplification sequence; or, (2) complementary or identical to a portion of a single-stranded amplification sequence. The Amplification Probes hybridize to the amplification sequence sufficiently adjacent to each other to enable the probes to be joined together. The Amplification Probe may or may not be modified at one or both ends for joining to other Amplification Probes. In addition, an Amplification Probe may or may not be modified by the incorporation of a means for controlling contamination.

Amplification Primer as used herein refers to a nucleic acid sequence which is complementary to an end portion of an amplification sequence and which is capable of acting as a point of initiation of synthesis of a primer extension product which is complementary to the amplification sequence. The primer extension product is formed in the presence of nucleotides and an agent for polymerization such as DNA polymerase. An Amplification Primer may or may not be modified by the incorporation of a means for controlling contamination.

Presynthesized probe or primer as used herein means an oligonucleotide sequence which has been synthesized prior to being added to a test sample reaction mixture.

Extending End of an amplification primer means the end of the amplification primer which is acted on by a polymerase to form extension product. The Extending End will be the 3'-end.

Amplification Product refers to the like copy and/or the complementary copy of an amplification sequence. The Amplification Product is synthesized in situ during an amplification procedure. Amplification Product may be the ligated nucleic acid sequence which is produced from ligation of a series of amplification probes which are contiguously hybridized to an amplification sequence. Amplification Product may also be the extension product of a polymerase chain reaction. The term Amplification Product includes modified amplification product.

Modified Amplification Product as used herein refers to amplification product which contains at least one modification site.

Modification Site refers to a single location into which has been incorporated a means for controlling amplification product contamination on an amplification product. A Modification Site includes, for example but without limitation, the introduction of a ligand, the introduction of an cross-linking agent or chemically cleavable site, and base change(s) to achieve an enzyme recognition site.

Contaminant Amplification Product is amplification product which is introduced into a test sample by a means other than amplification of the amplification sequence originally present in a test sample. The Contaminant Amplification Product may, for example, be the result of mechanical carryover or the result of airborne carryover contamination of a test sample with amplification product from a previously amplified sample or samples.

Complementary refers to sufficient complementarity to enable hybridization to occur. Complete complementarity is not required.

Substantially Complementary refers to complementarity wherein at least one base is mismatched.

Pseudo Restriction Site is a sequence of nucleic acid residues which but for the alteration of at least one nucleotide would represent a restriction enzyme recognition site. A Pseudo Restriction Site is not cleaved by a restriction enzyme that would recognize the unaltered sequence. Although the term "alteration" is used, Pseudo Restriction Sites are naturally occurring, and it will be appreciated that any nucleotide sequence not representing a restriction site will be a Pseudo Restriction Site.

A Preferred Pseudo Restriction Site is a pseudo restriction site which requires only one base modification to achieve a restriction enzyme recognition site.

Recognition Site as used herein means the specific sequence recognized by an enzyme, such as a restriction endonuclease or RNAse.

Enzyme Cleavage Site means the phosphodiester bond which is hydrolyzed by an enzyme, such as a restriction endonuclease or RNAse.

Remote Cutting Restriction Endonuclease, or Remote Cutter, is a restriction endonuclease that cleaves double-stranded DNA at a site outside of the enzyme recognition site.

The present invention is directed to a means for controlling carryover contamination from contaminant amplification product. A modified amplification product is created, as part of the amplification procedure, by incorporating at least one modification site into the amplification product such that the modified amplification product is distinguishable from target sequence. As a result of this modification, the modified contaminant amplification product can be selectively eliminated by removing, destroying, or otherwise rendering the modified amplification product nonviable as template sequence for subsequent amplification events. The means for selective elimination of modified amplification product will, of course, vary with respect to the particular modification incorporated into the amplification product.

It is possible to incorporate the contamination control method of the present invention into a pre-amplification treatment, a post-amplification treatment, or a combination of both pre- and post-amplification treatment of test samples. In the case of post-amplification treatment, modified amplification product is selectively eliminated from amplified test samples after the completion of the amplification procedure. This effectively minimizes the spread of the modified product throughout the laboratory or work space, where it can contaminate new test samples, thus producing false positives. Post-amplification treatment does not, however, completely eliminate the contamination problem, because some degree of airborne contamination will still occur through the simple process of opening the reaction tube to add the reagents (e.g., cutting agent) necessary to selectively eliminate the contaminant product.

In most cases, however, it will be possible, and in fact preferred, to "pre-treat" new test samples to selectively eliminate contaminant modified amplification product prior to subjecting the new test samples to amplification. In the case of pre-amplification treatment, modified amplification product may contaminate new test samples, with the contaminant amplification product being substantially completely removed or destroyed within the new test sample itself. Where the amplification reagents (e.g., amplification probes or primers) are susceptible to destruction by the same agent used to selectively eliminate the contaminant amplification product, it will be necessary to add the amplification reagents following pre-amplification treatment of the test sample. Where, however, the amplification reagents are resistant to destruction by the agent used to selectively eliminate the contaminant product (e.g., where certain types of remote restriction enzyme recognition modification sites or ribonucleotide substitutions are used), the destructive agent can be added to the test sample immediately prior to amplification; i.e., after all of the necessary reagents have been added to the test sample, thus providing the greatest degree of contamination control.

The method of the present invention enables carryover contamination to be controlled in an efficient, reliable, and economical manner. This is particularly important in a diagnostic setting where amplification procedures are routinely conducted. In these types of settings the same analyte is continually amplified over and over again, further exacerbating the problem of amplification product contamination of new samples. The longer the period of time over which a particular analyte is assayed, the greater the contamination problem. For example, the aspiration of only one $\mu l$ from a single 100 $\mu l$ sample, which has been amplified to 100 femtomoles of amplification product, will release 600 million copies of target into the air. If evenly dispersed in a typical work environment, this results in a concentration of approximately 350 molecules of contaminant amplification product for each cubic inch of work area.

The solution to carryover contamination provided by the present invention does not require the often elaborate and painstaking steps of prior art methods. For example, the present invention eliminates the need for the use of separate rooms for the introduction, amplification, and detection of new test samples. Likewise, the use of disposable clothes, costly positive displacement pipettes, and special disposable plumbing and sample handling devices are also unnecessary. The method provided herein has less inherent variation and does not contain the self-imposed limitations of prior art methods such as, for example, limitation of the amount of standard that is run alongside an amplification procedure. Many other advantages of the method of the present invention will be apparent to those skilled in the art.

The method of the present invention contemplates and embraces the introduction of a number of different types of modifications into the amplification product which is generated in an amplification procedure. What is important in the selection of a particular modification is that the modification provide a means for distinguishing and/or separating or destroying the amplification product from the target sequence in subsequently run test samples. In this way, contaminant amplification product is removed, destroyed, or otherwise rendered nonviable as a template for amplification prior to amplification of the target sequence in the treated new test sample.

The types of modifications useful in distinguishing contaminant amplification product will be apparent to those skilled in the art based upon the teachings of the present invention. These modifications may include, for example, the introduction of a ligand, the introduction of a cross-linking agent, or the introduction of an enzyme recognition site (including restriction enzyme recognition sites) or other suitable cleavable moiety. Certain of the modifications of the present invention will have a greater number of limitations than others, as will be more fully described. As a consequence, certain modifications will be preferred in certain situations, depending upon the characteristics of a particular analyte. The preferred modification for an amplification product in a given assay procedure will be apparent to persons of ordinary skill in the art, based upon the characteristics of the analyte to be amplified and the teachings of the present invention.

A modification is preferably incorporated into an amplification product by using presynthesized amplification probes or primers which contain the selected modification. Amplification with these modified probes or primers will, in turn, incorporate the modification(s) into the completed amplification product(s). Modification of the amplification probes or primers may be accomplished by any one of a number of methods that are known to those skilled in the art. In the case of ligands and other similar types of modifications, for example, the modification can be introduced into the completed oligonucleotide probe or primer following synthesis of the oligonucleotide. In the case of enzyme recognition sites, the modification(s) can simply be substituted into the oligonucleotide probe or primer during synthesis. It may also be possible, in the case of PCR, to amplify the target with polymerase in the presence of one or more modified nucleoside triphosphates to generate modified amplification product. (See, for example, Langer et al, *Proc. Natl. Acad. Sci. USA*, 78(11), 6633–6637 (1981).

The number of modification sites incorporated into the modified amplification product may also vary, although one site is usually sufficient to significantly reduce contamination. In most cases it is, in fact, preferred to incorporate only one modification site due to the expected reduction in efficiency of the amplification procedure from, e.g., steric hindrance (caused by the introduction of bulky moieties), interference with hybridization (caused by disruption of hydrogen boding between complementary nucleotides), or lack of complete complementarity of the amplification probes or primers to the target (caused by incorporation of restriction enzyme recognition sites). In this last case, however, it will be appreciated that the loss of cycling efficiency will primarily take place in the first cycle of amplification, where only amplification sequence having substantial complementarity with the modified probe (s) or primer (s) serves as template. Thereafter, the expected efficiency loss will diminish proportionately as the relative amount of amplification product acting as template (and having complete complementarity with the probes or primers) increases.

Where amplification product is not denatured following the final cycle of amplification, it is only necessary to modify one amplification probe or primer. In this case, the resulting modified amplification product will be double-stranded, enabling both strands to be removed or destroyed by way of a modification which is incorporated into only one strand. If, however, the test sample reaction mixture is subjected to a denaturing step following the final amplification cycle, both amplification primers and at least two opposite strand amplification probes (i.e., representing both the "upper" and "lower" strands of the probe pairs) may have to be modified in order to ensure that substantially all contaminant amplification product is rendered nonviable for subsequent hybridization.

Where a ligand has been introduced into the amplification product, the resulting ligand modified amplification product may be selectively eliminated by bringing the test sample containing the modified amplification product into contact with immobilized specific binding partner for the ligand. The immobilizing support is then removed along with bound ligand modified amplification product. Where the selective elimination is performed on a new test sample (i.e., prior to the initiation of an amplification procedure) the immobilized specific binding partner must be brought into contact with the new test sample before amplification probe or amplification primer reagents are added to the new test sample. If the new test sample reaction mixture is contacted after addition of these reagents, the modified probes or primers in the reagents will be pulled from solution along with the contaminant amplification product.

Figure 2:
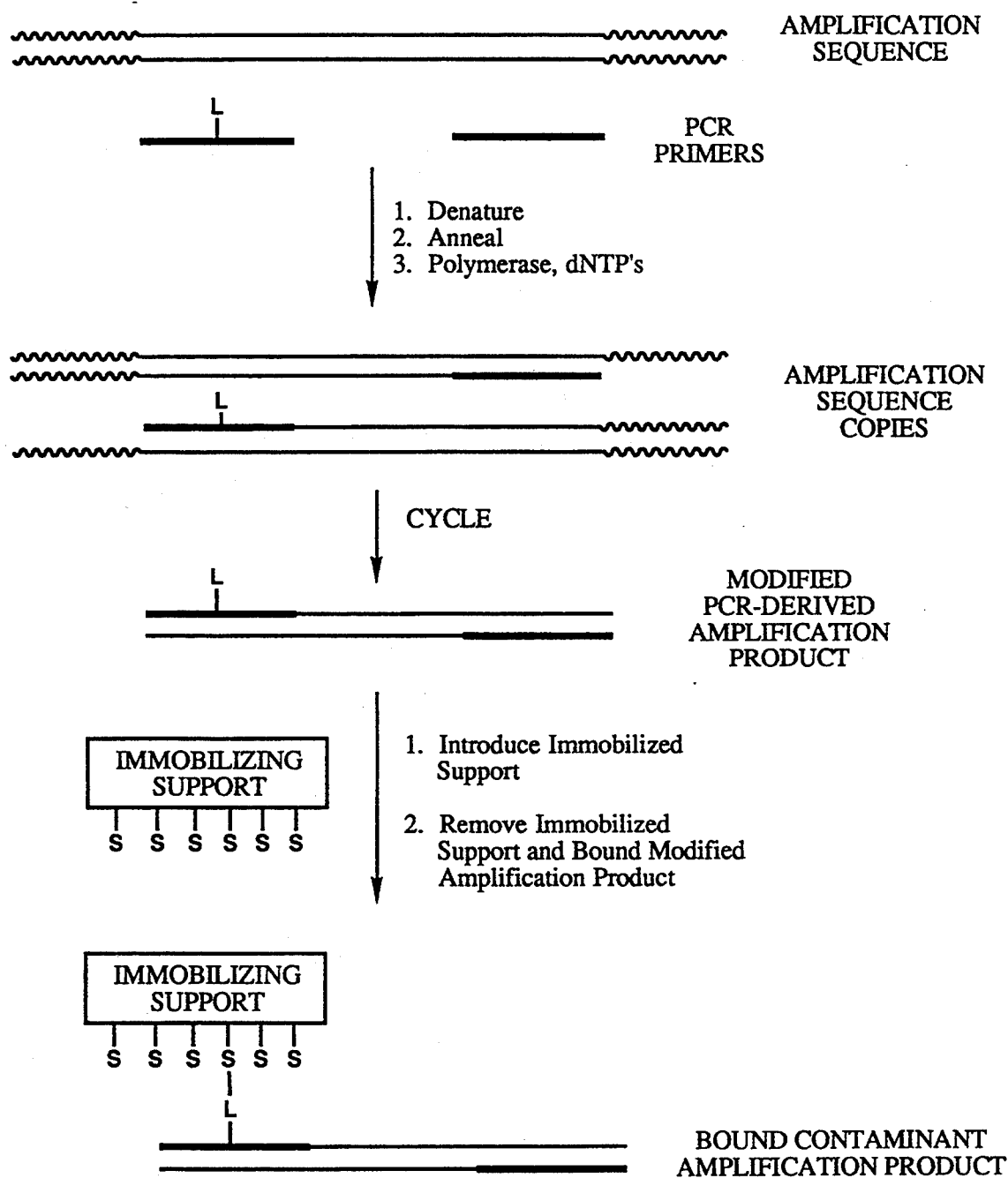
FIG. 2 is a diagram showing ligand modification of a PCR-derived amplification product and subsequent removal of the modified amplification product with immobilized specific binding partner.

The ligand which is incorporated as the modification will preferably be the smaller member of a specific binding pair, as this will minimize the reduction in amplification efficiency which is expected because of steric hindrance caused by the presence of the ligand on the amplification probes or primers. An example of a preferred ligand is biotin. Another preferred ligand is fluorescein. The ligand is introduced into at least one amplification primer, in the case of PCR, or into at least one amplification probe, in the case of LCR. FIG. 1 demonstrates a ligand modification of amplification product resulting from a ligase chain reaction type of amplification procedure (LCR-derived amplification product) and subsequent removal of the modified amplification product with immobilized specific binding partner for the ligand. FIG. 2 shows a similar scheme with respect to amplification product derived from a polymerase chain reaction (PCR-derived amplification product). The resulting biotin- or fluorescein-modified amplification product can be removed from subsequent test samples by contacting these samples with immobilized avidin or anti-fluorescein antibody, respectively.

In the ligand modification embodiment of the invention, it is preferred to modify the amplification probe(s) or primer(s) at a location on the probe or primer which will not interfere with the action of any enzyme or other reagent used in the amplification procedure; e.g., polymerase in the case of a PCR type of amplification procedure and ligase in the case of an LCR type of amplification procedure. In situations where polymerase can "read through" through the modification site in a PCR type of amplification procedure, the amplification primer can be modified at or about any location other than the extending end of the primer. Where, however, the polymerase cannot read through through the modification site, the PCR primer should be modified at its 5'-end.

Because LCR type amplification procedures do not employ a polymerase, enzyme read through limitations are not a concern in the location of ligand modification sites on the amplification probes. In the case of LCR, it is generally preferred to modify the amplification probe at any location other than the contiguous ends. For amplification probes which form an end segment of the amplification product, it will also be possible to modify these probes at their non-ligating ends. Otherwise, all amplification probes will preferably be modified somewhere near the center region of the probe.

The amplification probes or primers can be modified with the preferred fluorescein or biotin ligands using methods known to those skilled in the art. For example, the oligonucleotide probe or primer may be modified with ligand using a two-step process, wherein an amine group is first introduced during synthesis of the oligonucleotide. Following coupling, oxidation, deprotection, and removal of the oligo-amine primer or probe from the support used during synthesis, the ligand can be attached.

Another means for controlling carryover contamination from contaminant amplification product involves incorporating a covalently linked cross-linking agent into at least one of the amplification probes or primers used in an amplification procedure. The cross-linking agent of the resulting modified amplification product may be activated, either chemically or photochemically, to covalently cross-link the modified amplification product with complementary nucleic acid strands. The complementary nucleic acid strands may be from complementary modified or unmodified amplification product, or they may be in the form of carrier DNA if the modified amplification product has been denatured. In the latter case, however, both strands of the amplification product will have had to have been modified for substantially all of the resulting amplification product to be selectively eliminated.

Irreversibly cross-linking modified amplification product will render modified amplification product inert to any further amplification by preventing complete denaturation of the modified complementary amplification product after this point. In some cases there will be a risk of damaging the target nucleic acid in a new test sample by treating the sample with the appropriate activator for the cross-linking agent. This danger can be avoided, however, where the photo cross-linking groups have been made to absorb light at a wavelength which is not harmful to nucleic acid targets. Treatment of the new test samples must, however, proceed in the absence of new amplification probe reagents in order to destroy contaminant product without cross-linking the new reagents.

Figure 3:
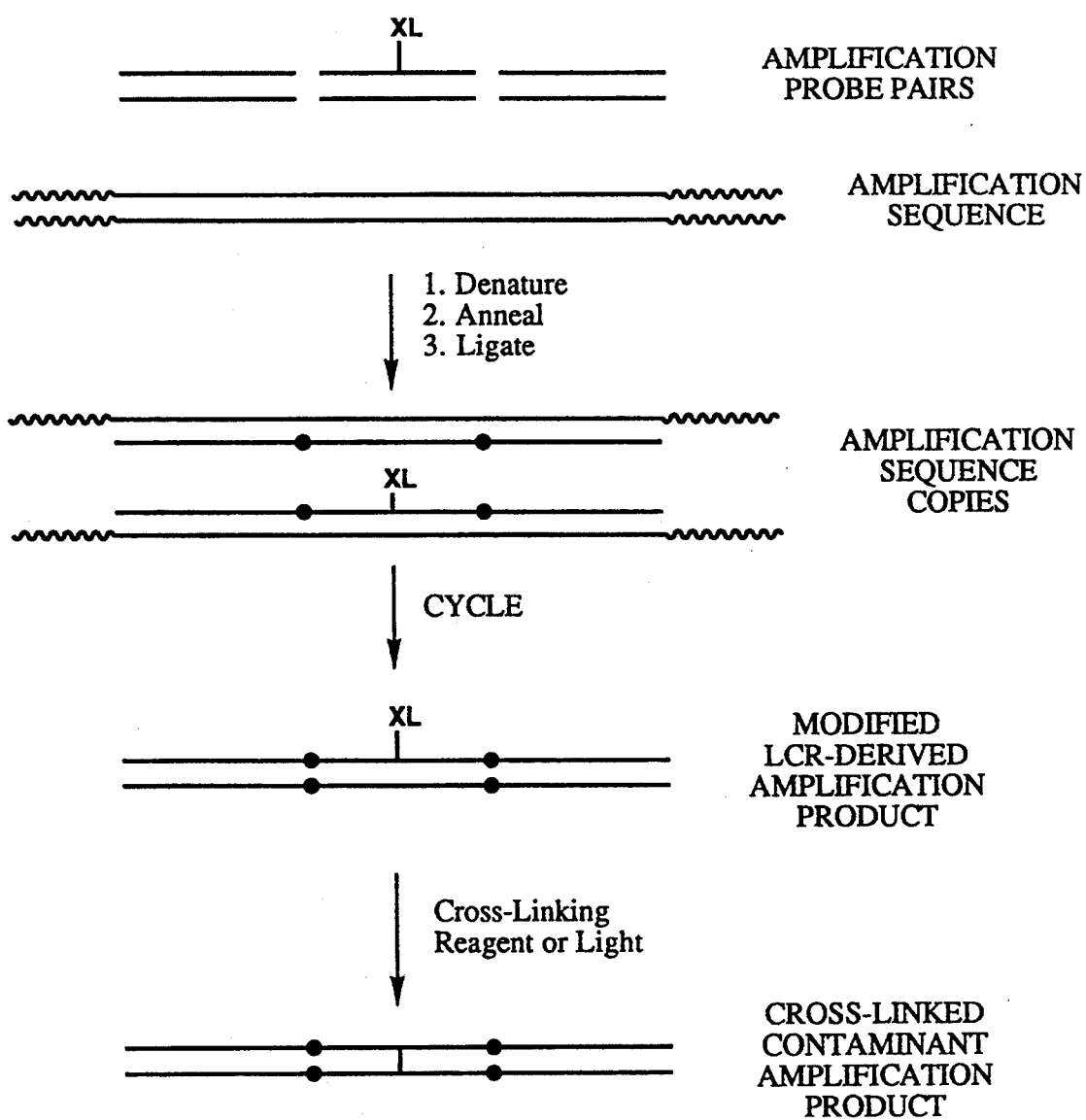
FIG. 3 is a diagram showing cross-linking agent modification of an LCR-derived amplification product and subsequent irreversible cross-linking of the modified amplification product.

The cross-linking agent is incorporated into the amplification probe(s) or primer(s) using methods known to those skilled in the art. In an LCR type of amplification procedure, it is preferred to locate the cross-linking agent on a middle amplification probe which will, in turn, incorporate the cross-linking agent nearest to the center of the resulting amplification product as is practically possible. With respect to the amplification probe carrying the cross-linking agent, it is further preferred to locate the cross-linking agent in the center region of the probe so as not to interfere with the joining or ligating of the ends of the modified probe. This is demonstrated in FIG. 3, wherein the cross-linking modification is incorporated into amplification product from one of the middle pair of probes of a three pair set of amplification probes.

Figure 4:
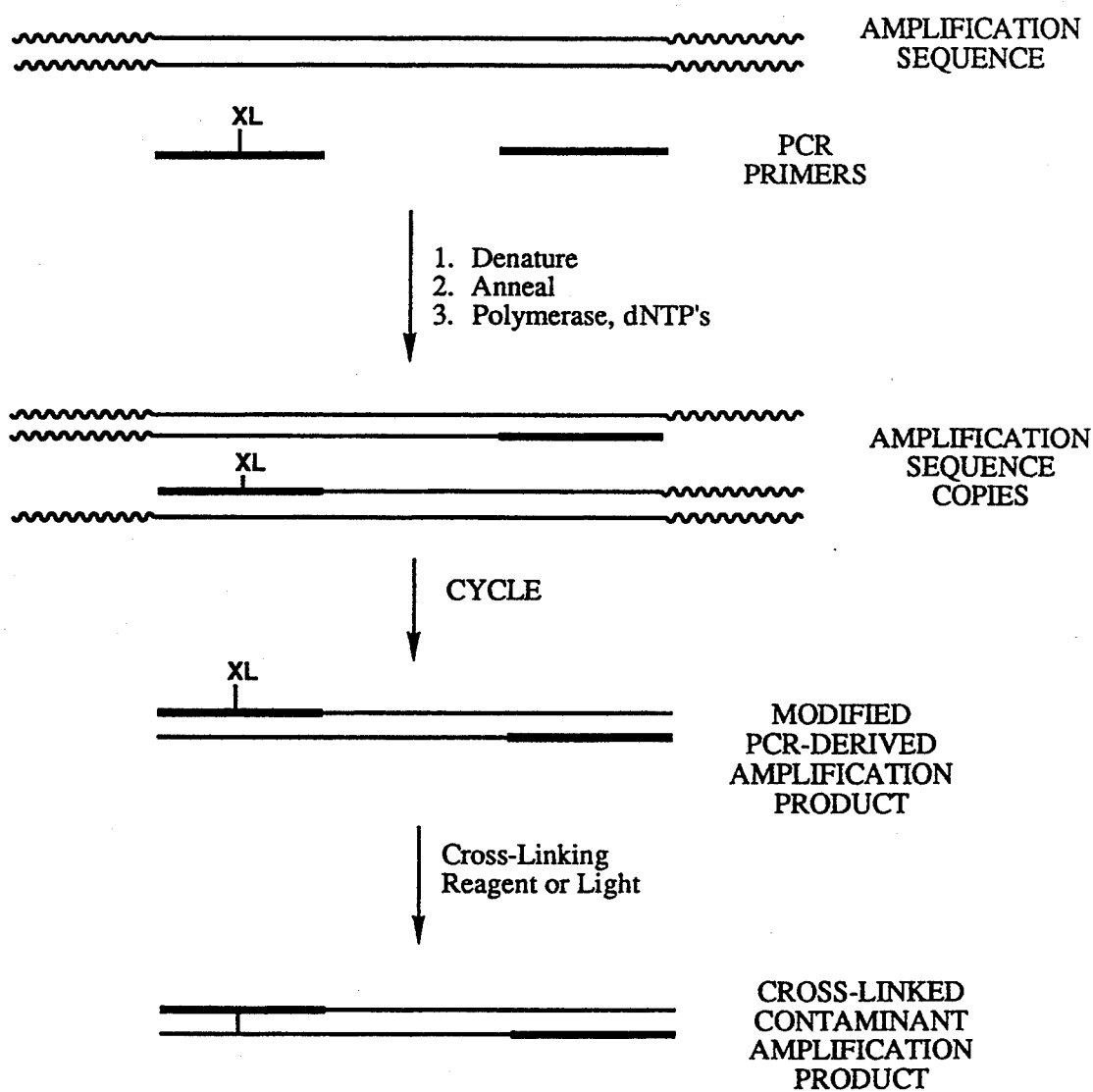
FIG. 4 is a diagram showing cross-linking agent modification of a PCR-derived amplification product and subsequent irreversible cross-linking of the modified amplification product.

In the case of a PCR type of amplification procedure, it is preferred to incorporate the cross-linking agent as close as possible to the extending end of an amplification primer without interfering significantly with the polymerase. As in the case of a ligand modification, if the presence of a cross-linking agent will interfere with the read through ability of the polymerase used for primer extension, the modification should preferably be placed at the 5'-end of the primer. FIG. 4 shows the incorporation of a cross-linking modification into PCR-derived amplification product using a presynthesized primer which has been modified at or about the middle of the primer.

It is more preferred, however, to modify the amplification product by incorporating at least one enzyme recognition site into the amplification product as the means for controlling carryover contamination. The enzyme recognition site may be introduced into the amplification product through the use of modified amplification reagents (e.g., modified amplification probes or primers). In PCR type amplification, it may also be possible to introduce the enzyme recognition site through the use of modified nucleoside triphosphates than can serve as both an enzyme recognition site and as a substrate for polymerases. The enzyme recognition modification site renders the resulting modified amplification product amenable to subsequent destruction by an enzyme which will selectively cleave the amplification product, but which will leave target or amplification sequence intact. Examples of enzyme recognition sites include, but are not limited to, restriction enzyme recognition sites and RNAse recognition sites.

As with other types of modifications, it is possible to incorporate a plurality of enzyme recognition modification sites into the amplification product. It is, of course, preferred to incorporate the enzyme recognition modification site(s) into the amplification product at a location, or locations, which, when cleaved, will result in the most complete destruction of the amplification product. The preferred placement for the enzyme recognition site will vary somewhat with respect to the analyte being sought, and will, in the case of restriction enzyme recognition sites be dictated to some degree, by the location and number of preferred pseudo restriction sites in the target sequence. Where only one enzyme recognition site is used to modify the amplification product, it will typically be preferred to place the enzyme recognition site as centrally to the completed amplification product as possible to achieve the most effective destruction.

Central placement of a single enzyme recognition site is more easily achieved with LCR-derived amplification product than with PCR-derived amplification product. This is because greater control is available in the construction of amplification product using presynthesized LCR amplification probes than is available with respect to the predominant portions of a PCR-derived amplification product which are necessarily synthesized in situ during amplification. For example, with PCR-derived amplification product, it will typically be necessary to place at least a part of the single enzyme recognition site on the amplification primer portion of the amplification product, rather than having the entire restriction site located somewhere in the polymerase extended portion which represents the vast central region of the completed amplification product. In contrast, a single enzyme recognition site can be readily introduced into the middle of amplification products using an LCR type of amplification procedure.

Additional limitations present themselves with respect to placement of a single enzyme recognition site on a PCR-derived amplification product. Most importantly, placement of a single enzyme recognition modification site most centrally to the completed amplification product will place the modification at the extending end of the amplification primer. Because this end of the primer is acted upon by the polymerase to form extension product in the PCR amplification procedure, the placement of a modification site at or near this location could potentially interfere with polymerase extension to form amplification product, and can therefore decrease the efficiency of amplification where the target sequence is acting as template sequence. Where, however, multiple enzyme recognition sites are desired, it may be possible to incorporate these multiple modification sites into the central (polymerase extended) portion of the resulting amplification product by employing one or more modified nucleoside triphosphates, such as, for example, a ribonucleotide triphosphate (recognized by an RNAse) in place of the corresponding deoxyribonucleoside triphosphate during amplification.

In order to carry out the method of the present invention using an enzyme recognition modification site recognized by RNAse, a selected portion of an amplification probe or primer is presynthesized using a series of RNA bases in place of the DNA bases which form the remainder of the amplification product. The series of RNA bases may be as little as one RNA base in length (in the case of RNAse A), or several bases in length (in the case of RNAse H), or the entire length of the amplification product. Unlike the incorporation of restriction enzyme recognition sites, RNAse recognition sites do not necessarily result in a loss of efficiency, because complete complementarity is not necessarily sacrificed in the latter case. Not only can complete complementarity exist with RNA base substitutions, but the RNA/DNA hybrid formation can be even stronger than for DNA/DNA hybrids. Preferred location(s) for the series of RNA bases will be apparent to those skilled in the art through minimal experimentation in light of the teachings of the present invention. It is generally preferred that the series of RNA bases be at least about one to three bases in length, depending upon the particular RNAse selected as the agent for selective elimination of the modified amplification product.

Different types of RNAse enzymes can be used to destroy the RNAse recognition modification site which is incorporated into the modified amplification product. A preferred RNAse is RNAse H. RNAse H is specific for RNA/DNA hybrids and will cut only the RNA bases in the duplex, leaving the DNA strand intact. Where RNAse H is used to destroy enzyme recognition site modified amplification product, it is important that the RNAse recognition site be incorporated into both strands of the modified amplification product, and further, that the location of the RNAse recognition sites be at different locations on the amplification product. In this way, the RNAse recognition site on each strand be located opposite a DNA strand of complementary amplification product, enabling the RNAse H to cut both strands of the modified amplification product duplex. Because the RNAse H enzyme will not cut RNA/RNA or DNA/DNA duplexes, contaminant amplification product which is carried over into a new test sample can be selectively eliminated without fear of inadvertently destroying DNA target sequence which may hybridize to modified amplification product.

Other types of preferred RNAse enzymes, reported to be specific for single-stranded RNA, include, for example, RNAse A, RNAse CL3, RNAse $T_2$, and RNAse $U_2$. Where these types of enzymes are used, there should be no danger of cutting target DNA. RNAse A is particularly preferred, because of its specificity for a single ribonucleotide substitution.

It is also possible to incorporate an enzyme recognition modification site that is recognized by a restriction enzyme. Each restriction enzyme modification site on the amplification product will be substantially complementary to a pseudo restriction site on the amplification sequence. It is preferred that the restriction enzyme site be introduced into amplification product with a minimal number of mismatches with respect to the target sequence. It is still more preferred that only one base be altered to introduce the recognition site; i.e., that the restriction enzyme recognition site be located opposite a preferred pseudo restriction site.

Selection of the restriction enzyme(s) and corresponding restriction enzyme modification site(s) in a particular amplification product will be influenced by a number of factors including the costs and availability of various restriction enzymes. It is also important and preferred to select an enzyme that has a high cutting efficiency with respect to the synthetic amplification product that is generated in an amplification procedure. Some restriction enzymes, for example, are believed to cleave synthetic oligonucleotide sequences much less efficiently than wild type sequences. The preferred restriction enzyme(s) for a given analyte and amplification system will be apparent to those skilled in the art based on the teachings of the present invention.

Incorporation of a restriction enzyme modification site into an amplification product is preferably carried out by first selecting from within the target sequence an amplification sequence that contains at least one preferred pseudo restriction site. Where a number of preferred pseudo restriction sites are contained within the designated amplification sequence, more options will be available with respect to the location of the restriction site (s) modification on the modified amplification product. Before final selection of the restriction enzyme modification site(s) in the amplification product, it is important to screen the entire amplification sequence to confirm that there are no naturally occurring restriction sites in the amplification sequence which would be subject to the action of the restriction enzyme chosen for selective cleavage of the modified amplification product. If such naturally occurring sites exist, an alternate restriction enzyme modification site must be chosen, otherwise the amplification sequence will be destroyed along with the modified amplification product.

In general, restriction enzymes will be able to cleave only modified amplification product which is double-stranded. Therefore, the restriction site modified amplification product should not be denatured before contact with the appropriate restriction enzyme. It will, however, be necessary in certain detection systems to denature the amplification product. Where a detection system using complementary probes, as disclosed in International Publication No. WO 89/12696, is used it will still be possible to cut the denatured product, as long as the restriction site is incorporated into the detection probes and the resulting amplification probe/detection probe duplex is not denatured.

Figure 5:
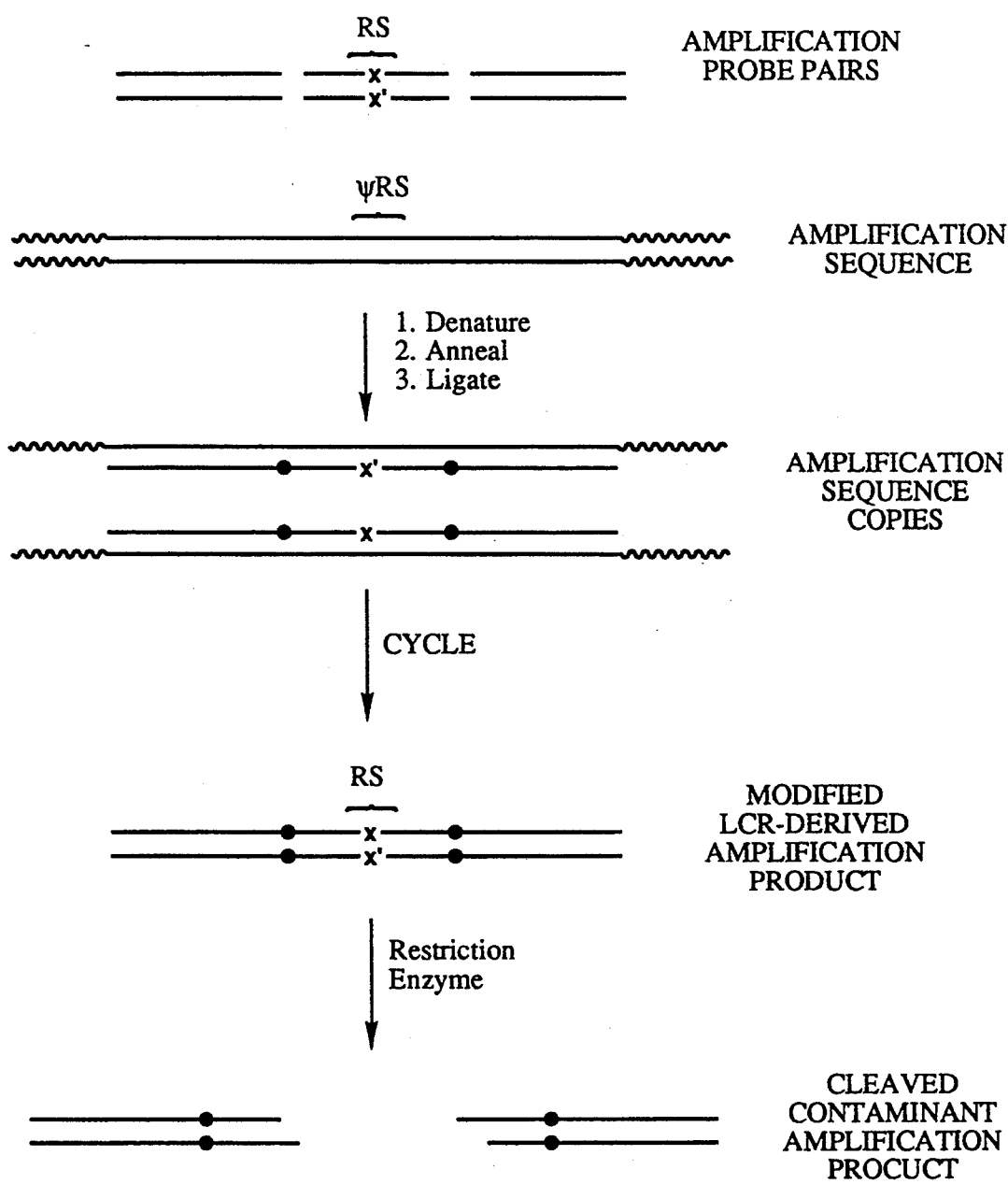
FIG. 5 is a diagram showing restriction site modification of an LCR-derived amplification product and subsequent cleavage of the modified amplification product with a restriction enzyme.

Modification of an LCR-derived amplification product with a single restriction enzyme modification site is shown in FIG. 5. In this diagram, three pairs of probes are ligated to form the amplification product, with the middle pair of probes being provided with the restriction enzyme recognition modification site. This results in LCR-derived modified amplification product which is susceptible to the action of a restriction enzyme which will destroy the modified amplification product by cutting it approximately in half. The amplification sequence of the target is resistant to the action of the enzyme, and remains in its native state. In this embodiment, however, new test sample must be treated to remove contaminant amplification product before the addition of new probe reagents, because pairs of modified amplification probes, necessary for the next amplification procedure, will also be destroyed.

Figure 6:
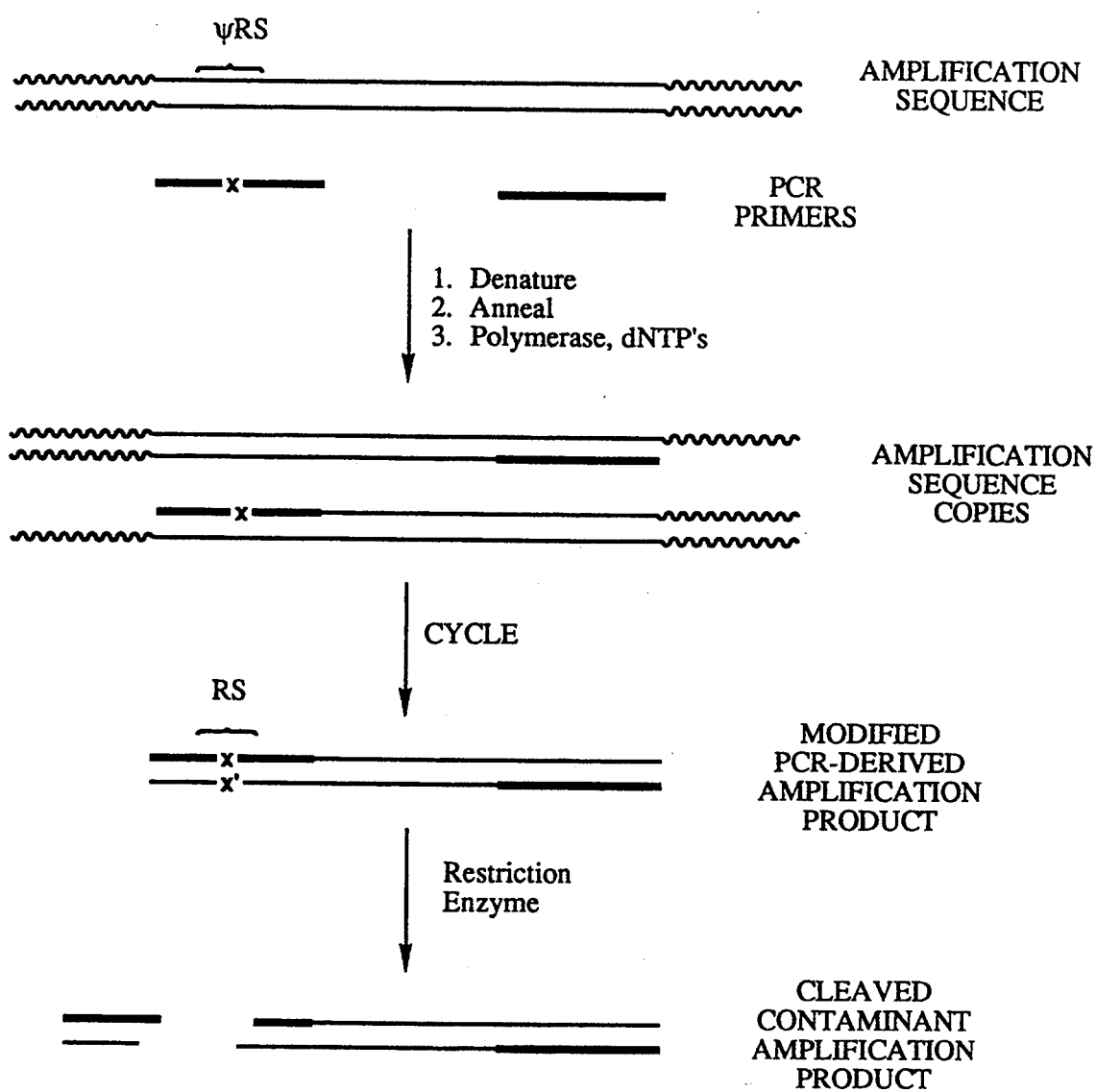
FIG. 6 is a diagram showing restriction site modification of a PCR-derived amplification product and subsequent cleavage of the modified amplification product with a restriction enzyme.
Figure 7:
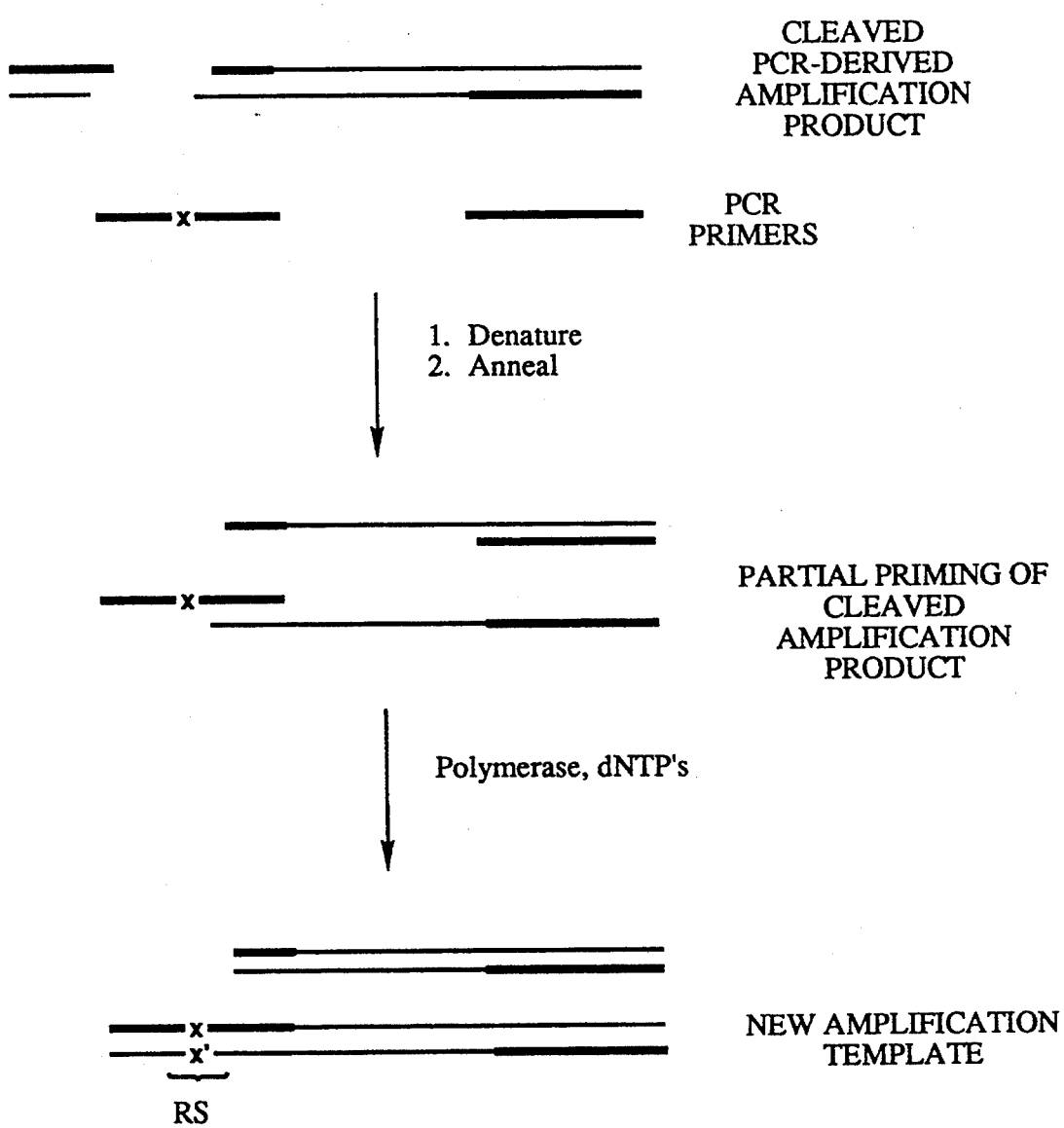
FIG. 7 is a diagram showing partial priming of a portion of restriction site modified PCR-derived amplification product which has been cleaved with a restriction enzyme.

FIG. 6 shows the same single site modification incorporated into an amplification primer used in a PCR type of amplification procedure. The resulting PCR-derived modified amplification product is susceptible to destruction with the same restriction enzyme, but in the case of the resulting PCR-derived amplification product, the cleavage takes place toward one end of the amplification product. The potential drawback to this uneven cutting of the PCR-derived product is shown in FIG. 7, which demonstrates partial priming of the cleaved PCR-derived amplification product in a subsequent amplification procedure. Partial priming occurs because the larger portion of the cleaved amplification product contains some of the complementary bases for the primer. Partial priming of cleaved PCR-derived contaminant amplification product in subsequent amplification procedures can still result in artificially high test sample results, including false positives.

Figure 8:
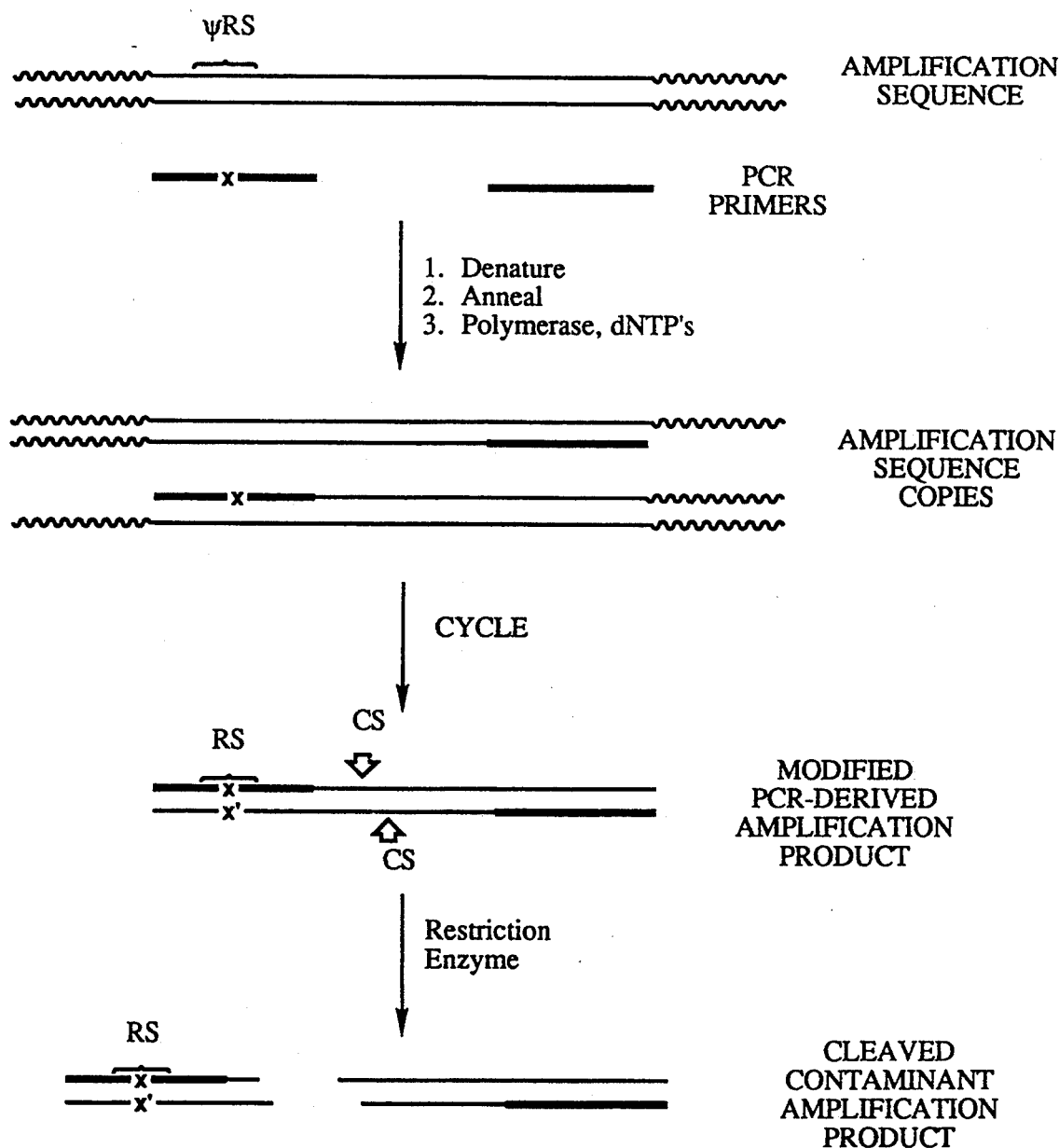
FIG. 8 is a diagram showing restriction site modification of a PCR-derived amplification product and subsequent cleavage of the modified amplification product with a remote cutting restriction enzyme.

Partial priming can be avoided in some instances if a restriction enzyme modification site can be incorporated sufficiently close to the extending end of the primer that the resulting recognition site actually occurs in the polymerase extended portion of the amplification product. This may, however, be difficult to achieve without interfering with the ability of the polymerase to initiate primer extension. Partial priming can preferably be eliminated by using remote cutting restriction enzymes and incorporating the appropriate corresponding restriction modification sites into the modified amplification products of a PCR type of amplification procedure. The incorporation of a remote cutting restriction enzyme recognition site into a PCR-derived amplification product is shown in FIG. 8. In this instance, the remote cutting restriction enzyme recognition site is incorporated into the presynthesized amplification primer, but the actual cleavage by the restriction enzyme takes place in the extended portion of the completed amplification product. As a result, the destroyed PCR-derived amplification product cannot participate in subsequent amplification events, because there is no opportunity for partial priming to occur.

Figure 9:
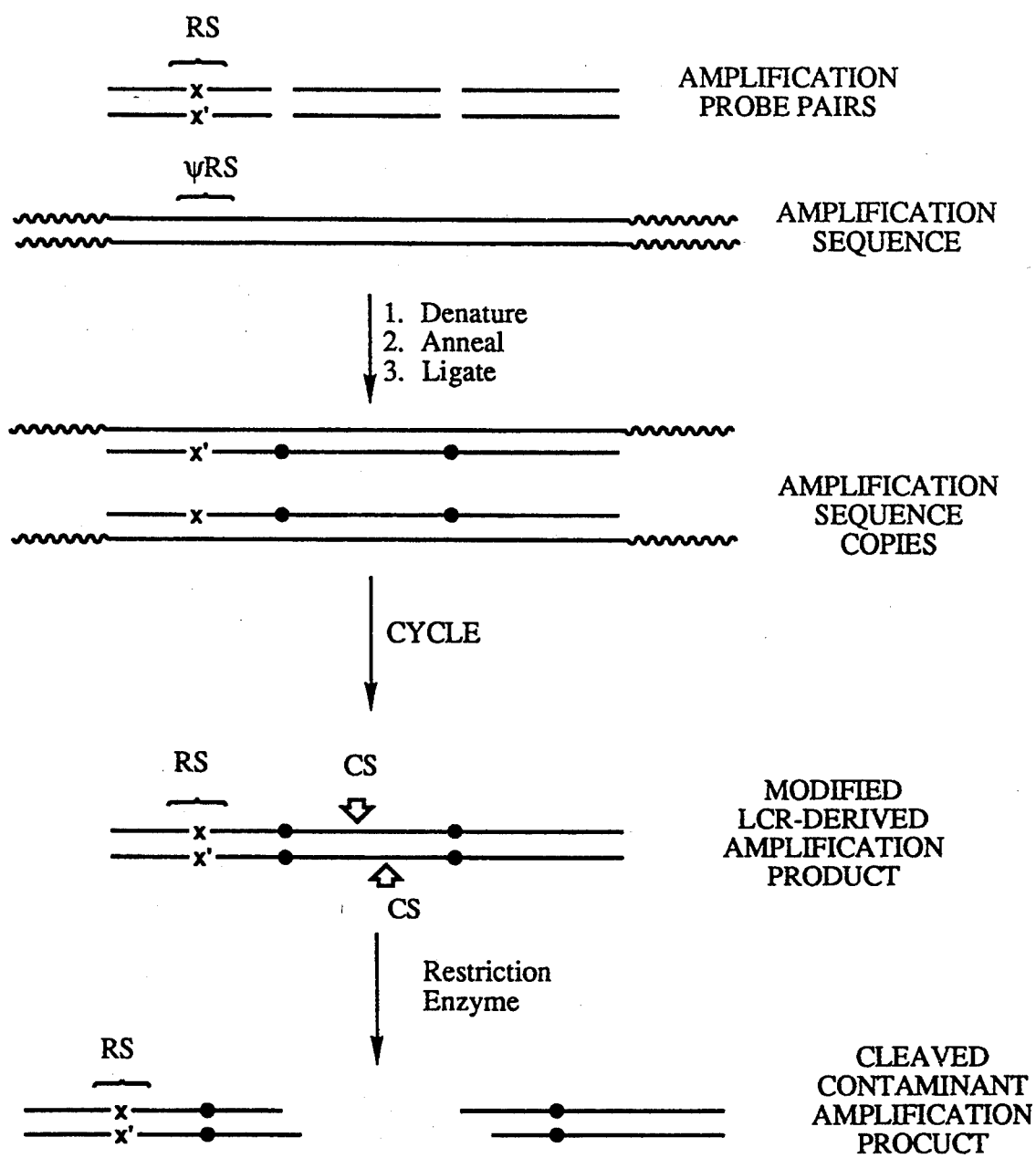
FIG. 9 is a diagram showing restriction site modification of an LCR-derived amplification product and subsequent cleavage of the modified amplification product with a remote cutting restriction enzyme.

Remote cutters can also be useful, and in some cases preferred, in the modification of LCR-derived amplification product. Where the recognition site and corresponding cleavage site can be located on regions of amplification product represented by different pairs of probes, it will be possible to contact a new test sample with restriction enzyme even after the addition of the amplification probe reagents to samples containing target without danger of cleaving the probes at the same time as the contaminant amplification product is destroyed. FIG. 9 shows the incorporation of a remote cutting restriction enzyme recognition site into one of the end pairs of a three pair set of probes such that the completed LCR-derived amplification product will be cleaved at a position approximating the middle of the completed product. In this case, the cleavage site corresponds to the portion of the completed amplification product represented by the middle pair of amplification probes.

It is still further possible to introduce a chemically cleavable site into an amplification product by modifying the nucleic acid backbone of the amplification probes or primers that are used in an amplification procedure. It is more preferred to use this embodiment in an LCR type of amplification procedure than in a PCR type of amplification procedure, because the presence of a chemically cleavable site is likely to interfere with the read through ability of some polymerases. The modified amplification product containing the chemically cleavable modification site can be destroyed by treatment with a reagent that cleaves at the modification site(s). The incorporation of a chemically cleavable moiety may be able to alleviate the problem of reduced cutting efficiency observed in some of the restriction enzymes with respect to synthetic sequences, since chemical cleavage reactions are not based on a biologically active enzyme, and therefore do not distinguish between synthetic and wild type nucleic acids. Further, most chemically cleavable moieties will be cut regardless of whether the modified amplification product is double-stranded or single-stranded.

In this embodiment, the cleavable sites can be incorporated into presynthesized probes or primers using commercially available reagents as shown in FIG. 10. Partial probe or primer sequences are first synthesized to contain amine groups on the 3'- or 5'-ends of the partial sequences. These amine-labeled ends are subsequently joined with a homobifunctional linking reagent to form the complete, but interrupted, sequence which is used as the amplification probe or primer. For example, it is possible to use DSP (dithiobis[succinimidylpropionate]), DST (disuccinimidyl-tartarate), or EGS (ethylene glycolbis[succinimidyl-succinate]) (shown in FIG. 10) to join together the 3'- and 5'-labeled ends of the partial probe or primer sequences, thus forming the complete probe reagents containing the cleavable site. In this instance, the modified amplification product generated with these probes or primers can be destroyed by cleavage with a reducing agent such as dithiothreitol (where DSP is used as the homobifunctional linking agent), an oxidizing agent such as sodium periodate (where DST is used), or hydroxylamine (where EGS is used).

It will be preferred to locate the chemically cleavable modification site near the middle of an amplification probe or primer so that disruption of hybridization will be minimized. It is possible to construct the modified amplification probes or primers so that these reagents are either completely complementary (the cleavable moiety is contained in a "loop-out") or substantially complementary (the cleavable moiety is substituted for one of the nucleotides in the probe sequence) to the amplification sequence. In certain instances, such as where a ribonucleotide substitution provides the chemically cleavable moiety, the reagents will be completely complementary with the amplification sequence without the requirement of a loop-out.

Ribonucleotide substitution simultaneously imparts both an enzyme recognition site and a chemically cleavable site to the resulting modified amplification product through the incorporation of the same labile bond. This modified amplification product is labile to either or both: (1) strong base (chemical cleavage); and, (2) certain RNAses (enzymatic destruction). In either case, the resulting cleavage products can no longer function as templates for amplification.

These labile bonds are preferably incorporated into the modified amplification product using amplification probes or primers containing a single ribonucleotide substitution on their respective 3'-ends. In the case of PCR, both of the amplification primers will contain the ribonucleotide substitution. In the case of LCR, at least one upper strand and one lower strand amplification probe will contain the ribonucleotide substitution. Because the ribonucleotide substitution occurs on the 3'-ends of the primers and probes, the labile bonds of the modified amplification product are actually created in situ during amplification. As a result, the amplification reagents do not contain the labile bond (i.e., are not base labile), thus enabling carryover contamination to be destroyed by treatment with a strong base or an RNAse in the presence of these treatment-resistant reagents without affecting their integrity to amplify. Furthermore, the ability of the wild type target to serve as a template for amplification is likewise unaffected by the base or RNAse treatment, enabling destruction of the labile carryover contaminant amplification product to take place in the presence of both the target and the amplification reagents in a new test sample.

There are two important requirements for generating PCR- or LCR-derived modified amplification product from modified amplification primers or probes containing a ribonucleotide substitution. First, the enzyme required for formation of the amplification product must operate effectively in the presence of the substitution. In the case of PCR, polymerase must extend off of one of the hydroxyl groups on the 3'-ends of the hybridized primers. In the case of LCR, ligase must catalyze the covalent joining of a 3'-ribose group of one oligonucleotide probe to the 5'-phosphate group of another oligonucleotide probe. Second, the resulting modified amplification product (which contains one or more internal ribonucleotides) must serve as a viable template for subsequent cycles of amplification. (I.e., in the case of PCR, polymerase must read through the ribonucleotide linkage.)

The method of the present invention is not limited to LCR and PCR types of amplification procedures, but can be employed to control contamination problems encountered in other types of amplification procedures, such as, for example, transcription types of amplification procedures and repair chain reaction amplification.

The present invention further provides kits for the reduction of carryover contamination in an amplification procedure. The kits may take the form a kit for use in a PCR-type amplification procedure or a kit for use in an LCR-type amplification procedure. In the case of a kit for PCR-type amplification, the kit will contain: (1) at least one modified amplification primer which is capable of incorporating at least one modification site into a PCR-derived amplification product such that the resulting modified PCR-derived amplification product is distinguishable from target sequence; and, (2) a means for selectively eliminating the modified PCR-derived amplification product. In the case of a kit for LCR-type amplification, the kit will contain: (1) at least one upper strand and at least one lower strand modified amplification probe which is capable of incorporating at least one modification site into an LCR-derived amplification product such that the resulting modified LCR-derived amplification product is distinguishable from target sequence; and, (2) a means for selectively eliminating the modified LCR-derived amplification product.

In the case of either PCR-type amplification or LCR-type amplification, the modification may be an enzyme recognition site and/or a chemically cleavable site. The means for selectively eliminating the modified amplification product may be an enzyme (in the case of an enzyme recognition site) or a strong base (in the case of a chemically cleavable site). Certain modifications, such as an RNA base substitution, may form both an enzyme recognition site (RNAse) and a chemically cleavable site (strong base). Other enzyme recognition sites include restriction enzymes, including remote cutting restriction enzymes.

The following examples are provided to aid in the understanding of the present invention, the true scope of which is set forth in the appended claims. It is understood that modifications can be made in the procedures set forth, without departing from the spirit of the invention.

In order to demonstrate the efficacy of the present invention, several different synthetic nucleic acid sequences were used to simulate: (1) amplification sequences; (2) amplification products; (3) modified amplification products; (4) amplification probes; (5) detection probes; (6) amplification primers; (7) detection primers; and, (8) a polylinker used to determine cutting efficiencies of restriction enzymes on synthetic nucleic acid sequences. These synthetic sequences are shown in FIGS. 11, 13, 16, 20, 23, and, 28.

EXAMPLE 1

Preparation of Synthetic Sequences

The synthetic amplification sequences (AS), amplification probes (AP), chemically phosphorylated amplification probes (pAP), detection probes (DP), chemically phosphorylated detection probes (pDP) (shown in FIG. 11), and the polysite DNA (shown in FIG. 13) were synthesized using an Applied Biosystems model 380B synthesizer (Applied Biosystems, Inc., Foster City, Calif.), as disclosed in International Publication No. WO 89/12696.

Polymer-bound dimethoxytrityl-protected nucleoside (first nucleic acid in sequence) in support columns was first stripped of its 5'-dimethoxytrityl protecting group by passing a solution of 3% trichloroacetic acid in dichloromethane through the column for one minute. The polymer was then washed with acetonitrile, followed by rinsing with dry acetonitrile. The polymer, containing the deprotected nucleoside, was then placed under argon prior to proceeding to the next (condensation) step.

The condensation step was carried out by first treating the polymer with tetrazole in acetonitrile. The polymer-bound deprotected nucleoside was then reacted with a protected cyanoethyl nucleoside phosphoramidite (second nucleic acid in sequence; ABI, Foster City, Calif.) in acetonitrile. The condensation reaction was allowed to proceed for 2.0 minutes, with the reactants being subsequently removed by filtration.

Condensation was followed by capping the unreacted 5'-hydroxyl groups of the nucleosides by passing a solution prepared by mixing one part of a mixture available from ABI (Foster City, Calif.) containing acetic anhydride and 2,6-lutidine in THF (tetrahydrofuran) and one part 1-methylimidazole in THF (also available from ABI, Foster City, Calif.) through the column for one minute.

Following removal of the capping solution, the polymer was treated for 1.5 minutes with an oxidizing solution (0.1 M $I_2$ in $H_2O$/2,6-lutidine/THF, 1:10:40). This was followed by an acetonitrile rinse. The cycle began again with a trichloroacetic acid-methylene chloride deprotection and was repeated until the desired oligonucleotide sequence was obtained.

The polymer-bound final oligonucleotide chain was treated with fresh concentrated ammonia at room temperature for 2.0 hours. After decanting the solution from the polymer, the concentrated ammonia solution was heated at 60° C. for 16 hours in a sealed tube.

Each oligonucleotide solution was extracted with 1-butanol and ethyl ether. The concentration of each extracted solution was determined spectrophotometrically by measuring absorption at 260 nm. An aliquot of each extracted solution containing 5.0.O.D. units of synthesized oligonucleotide was concentrated for preparative electrophoresis and loaded into a 15% polyacrylamide 7 molar urea gel. After electrophoresis, the product band was visualized by U.V. electrophoresis, cut from the gel, extracted with elution buffer (300 mM sodium acetate (NaOAc), 2,5 mM EDTA, 100 mM Tris.HCl, pH 8.0), and then desalted on a G-50 sephadex® (Pharmacia LKB Biotech, Inc., Piscataway, N.J.) column using TEAB eluant (triethyl ammonium bicarbonate) to yield the purified oligonucleotide.

The oligonucleotides were chemically phosphorylated using a phosphorylating reagent available from Glen Research Corporation (Herndon, Va.), Catalog No. 10-1900-90. This reagent was first described by T. Horn and M. Urdea, *Tetrahedron Lett.*, 27, 4705–4708 (1986), and can be used with standard phosphoramidite automated synthesis protocols. Automated oligonucleotide synthesis on the Applied Biosystems instruments proceeded in the 3'→5' direction with the chemical phosphorylating agent being conveniently introduced at the last cycle of synthesis. Phosphorylation efficiency was quantitated through the measurement of the amount of dimethoxyltrityl group liberated after the last cycle. Standard deprotection, cleavage, and purification procedures were used to isolate the desired 5' chemically phosphorylated oligonucleotides.

EXAMPLE 2

Single Restriction Site Modified Amplification Product

Introduction of Restriction Site Modification into Amplification Product

This example demonstrates the introduction of restriction enzyme modification sites into amplification products in an LCR type of amplification procedure. The introduction of restriction enzyme modification sites in this example was accomplished by using presynthesized amplification probes containing restriction enzyme modification sites to amplify an amplification sequence containing corresponding preferred pseudo restriction sites. The restriction enzyme modification sites were selected so that each of the six amplification probes (i.e., three pairs) contained a restriction enzyme modification site and also contained a single base mismatch with respect to the amplification sequence (i.e., would hybridize opposite a preferred pseudo restriction site in the amplification sequence).

It was also desired to show the selective elimination of restriction enzyme modified amplification product by demonstrating that the resulting modified amplification products containing the restriction enzyme modification sites amplify very inefficiently (i.e., are substantially destroyed) following treatment with the appropriate restriction enzyme, while the amplification sequences containing the corresponding pseudo recognition sites are unaffected following treatment with the same restriction enzyme.

Although the modified amplification product ($AMP_1$) was constructed to contain one Hae III and two Bbv I restriction endonuclease sites, only the Hae III site was used as the selected modification to demonstrate cleavage of the amplification product. The amplification sequence (AS) differs from the amplification product with respect to only three base pairs which are introduced into the amplification product ($AMP_1$) through the three pairs of amplification probes ($AP_1$/$pAP_1'$, $pAP_2$/$pAP_2'$, and $pAP_3$/$AP_3'$), each containing one of the three base pair differences. The amplification sequence contains the corresponding pseudo restriction sites for the restriction endonuclease sites incorporated into the amplification product.

A. Restriction Endonuclease Digest of Amplification Sequence, Modified Amplification Product, and Carrier DNA In order to determine the effectiveness of restriction enzyme cleavage of amplification product to destroy its ability to serve as a template in subsequent amplification procedures, the following restriction endonuclease reactions were set up in a final volume of 100 μl of buffer containing: 0.05 mg/ml BSA (bovine serum albumin), 50 mM Tris.HCl, 6.6 mM MgCl$_2$, 6.6 mM DTT (dithiothreitol):

Reaction 1: 2 femtomoles AMP$_1$+20 units active Hae III restriction enzyme

Reaction 2: 2 femtomoles AMP$_1$+20 units heat inactivated Hae III restriction enzyme Reaction 3: 2 femtomoles AS+20 units active Hae III restriction enzyme Reaction 4: 2 femtomoles AS+20 units heat inactivated Hae III restriction enzyme Reaction 5: 1 μg human placental DNA+20 units active Hae III restriction enzyme Reaction 6: 1 μg human placental DNA+20 units heat inactivated Hae III restriction enzyme All six reactions were incubated at 37° C. for 16 hours, followed by 90° C. for 10 minutes to destroy any remaining Hae III activity.

B. Amplification of Synthetic Amplification Sequence and Restriction Site Modified Amplification Product Following Treatment with Active and Inactive Hae III Restriction Enzyme Amplification sequence (AS), restriction enzyme recognition site modified amplification product (AMP$_1$), and human placental DNA (HP-DNA) from the above six reactions were amplified in duplicate in a 15 cycle LCR type amplification procedure using 3 pairs of amplification probes (AP$_1$pAP$_1$', pAP$_2$/pAP$_2$', and pAP$_3$/AP$_3$'), as shown in FIG. 5. It should be noted that these probes will have three base pair mismatches with the amplification sequence, but will be completely complementary with AMP$_1$.

Many different types of ligases can be used to effect ligation of the contiguously hybridized probes in an LCR type of amplification procedure. For example International Publication No. WO 78/12696 discloses the use of E. coli ligase (available, e.g., from New England Biolabs, Inc., Beverly, Mass.) to ligate the amplification probes. It is generally preferred, however, to use a thermal stable ligase (TSL) in order to avoid the requirement for continual addition of fresh ligase reagent with each LCR amplification cycle. In this example, thermal stable HB8 DNA ligase isolated from Thermus thermophilus (AACC #27634), obtained as a gift from Miho Takahashi (Mitsubishi-Kasei Institute of Life Sciences, Protein Chemistry Laboratory, 11 Minamiooya, Machida-shi, Tokyo 194, Japan) was used to ligate the amplification probes throughout the amplification cycling.

Thermal stable DNA ligase buffer (TSLB) was prepared at 10× concentration to contain 500 mM Tris.HCl (pH 7.6), 66 mM MgCl$_2$, 10 mM EDTA (ethylenediaminetetraacetic acid), 66 mM DTT, and 500 μg/ml BSA.

Loading Buffer was prepared to contain 11.8 mM EDTA, 6.3 M urea, 0.02% bromophenol blue, and 0.02% xylene cyanole.

One hundred attomoles of DNA from each of the reactions 1 through 4 and 5 ng of HP-DNA from each of the reactions 5 and 6 were amplified in duplicate using a Perkin-Elmer/Cetus Thermocycler (Perkin-Elmer Corporation, Norwalk, Connecticut). Each amplification reaction was started in a volume of 50 μl of 1× TSLB containing 2 picomoles of each amplification probe (AP$_1$/pAP$_1$', pAP$_2$/pAP$_2$', and pAP$_3$/AP$_3$'), 0.03 units of TSL, and 66 μM NAD in 0.5 ml Eppendorf ® tubes. Two drops of mineral oil were added to each reaction tube to prevent evaporation during thermocycling. The amplification reactions were cycled 15 times by heating to 90° C. for 2 minutes and 50° C. for 5 minutes for each cycle.

C. Detection of Restriction Site Modified Amplification Product

The amplification products from Example 1B were detected using a two probe detection system as described in International Patent Application No. 89/02649, using the previously described HB8 DNA ligase and TsLB buffer in place of the E. coli ligase and E. coli ligase buffers of International Patent Application No. 89/02649. The detection probes DP$_1$ and pDP$_2$, shown in FIG. 11, were used to detect the amplification product.

EDTA/dye reagent was prepared to contain 20 mM EDTA, 6.1 M urea, 0.02% bromophenol blue, and 0.02% xylene cyanole.

Capture buffer, 1× in SSPE and 0.01% in ATC (alkaline-treated casein; Livesay, J. H. and R. A. Donald, Clin. Chira. Acta, 123, 193 (1982)), was prepared by dissolving 8.7 g NaCl, 1.38 g NaH$_2$PO$_4$.H$_2$O monobasic, 370 mg EDTA, and 100 mg ATC in 800 ml H$_2$O. The solution was adjusted to pH 6.8 with 5 N NaOH, after which the volume was brought up to 1 L.

In order to provide a means for subsequent visualization of the modified amplification products by autoradiography, detection probe DP1 was phosphorylated with $\gamma^{32}$p-ATP and polynucleotide kinase (Boehringer Mannheim Biochemicals, Indianapolis, Ind.) using radioactive phosphorus at a specific activity of approximately 7000 Ci/mmole. Excess $\gamma^{32}$p-ATP was separated from the phosphorylated oligonucleotide by gel filtration through G50/50 Sephadex ® (Pharmacia, Uppsala, Sweden).

Figure 12:
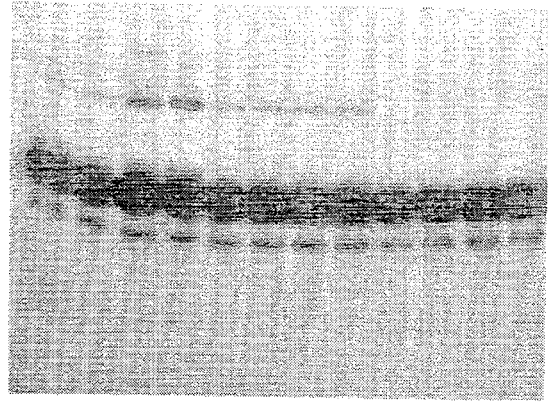
FIG. 12 is a photograph of an autoradiogram showing the relative amplification efficiencies of target and restriction enzyme modified amplification product following treatment of both the target sequence and the modified amplification product with restriction enzyme.

The detection reactions were prepared in a final volume of 16 μl of 1× TSLB and contained one-tenth of the amplification reaction mixtures, 200 femtomoles of each detection probe ($\gamma^{32}$P-DP$_1$ and PDP$_2$), 0.03 units of TSL, and 66 μMNAD. The detection reactions were completed by heating to 90° C. for five minutes and then to 50° C. for ten minutes. The reactions were then stopped by addition of an equal volume of Loading Buffer, followed by heating at 90° C. for an additional three minutes. The products were separated by electrophoresis of the reaction mixtures on denaturing 15% polyacrylamide gel and visualized by autoradiography. (See FIG. 12.) Relative amplification efficiencies were estimated based on laser densitometer traces on an LKB UltroScan ™ XL (Pharmacia LKB Biotech, Inc., Piscataway, N.J.).

Cleaved amplification product (Reaction 1, Lanes 1 and 2) amplified only 7% as efficiently as uncleaved amplification product (Reaction 2, lanes 3 and 4). This corresponds to an effective reduction in contaminant amplification product by 93%.

Cleaved (Reaction 3) and uncleaved (Reaction 4) amplification sequence (lanes 5 and 6, and 7 and 8, respectively) amplified with nearly identical degrees of efficiency. This demonstrates that amplification sequence containing pseudo restriction enzyme recognition sites is not affected by treatment with the same restriction enzyme that destroys the corresponding modified amplification product.

Cleaved (Reaction 5) and uncleaved (Reaction 6) carrier HP-DNA (lanes 9 through 12) showed no signal, indicating that the signals in lanes 1 through 8 are not due to any non-specific interactions with DNA or other components in the reaction mixtures.

It should be noted that uncleaved amplification sequence (AS, Reaction 4, lanes 7 and 8) amplifies only 18% as efficiently as uncut amplification product (AMP$_1$, Reaction 2, lanes 3 and 4). This is most likely due to the fact that the amplification probes contain three mismatches with respect to the amplification sequence and are completely complimentary only to the amplification product.

EXAMPLE 3

Evaluation of Remote Cutting Enzymes

It will be appreciated that the modified amplification product from Example 2 could also have been cleaved with Bbv I remote cutting restriction enzyme In this case, amplification probes AP$_1$/pAP$_1$', pAP$_2$/pAP$_2$', and pAP$_3$/AP$_3$' from Example 2 would not be cleaved by the Bbv I enzyme. Other remote cutting restriction enzymes can also be used to cleave correspondingly modified amplification product from either PCR or LCR types of amplification procedures.

In order to identify remote cutting enzymes with relatively high degrees of cutting efficiencies, eight different enzymes, purchased from New England Biolabs, Inc. (Beverly, Massachusetts) were selected for evaluation for potential use as remote cutters in the restriction enzyme recognition modification site of the present invention. A 42 base double-stranded sequence of DNA was designed to contain restriction enzyme recognition sites for all eight of the remote cutting restriction enzymes, as shown in FIG. 13. The upper and lower strands for this polysite DNA sequence were synthesized using an Applied Biosystems model 380B synthesizer (Applied Biosystems, Inc., Foster City, Calif.), as described in Example 1. These complementary sequences were allowed to hybridize to form the double-stranded sequence for remote cutter evaluation. Equimolar amounts of the upper and lower strands of the polysite DNA were added together and briefly heated to 90° C. and then allowed to cool to room temperature to form double-stranded DNA suitable for restriction endonuclease cleavage. Twenty picomoles of the double-stranded polysite DNA was labeled with $\gamma$-$^{32}$p at both 5'-ends, as described for $\gamma$-$^{32}$P-DP1 in Example 2.

The polysite DNA was then subjected to cleavage by the selected eight restriction enzymes using eight individual reactions containing 200 femtomoles of the $^{32}$P-labeled polysite DNA, 1× buffer, and one of the following enzymes in a total reaction volume of 50 µl:

| Reaction | Restriction Enzyme | Amount of Restriction Enzyme (Units) | Buffer |
|---|---|---|---|
| 1 | ALW I | 4 | 1x TSLB |
| 2 | Bbv I | 2 | 1x TSLB |
| 3 | BspM I | 4 | 1x TSLB* |
| 4 | Fok I | 8 | 1x TSLB |
| 5 | Ple I | 1 | 1x TSLB |
| 6 | Hga I | 8 | 1x TSLB |
| 7 | Hph I | 0.8 | 1x TSLB |
| 8 | SfaN I | 3 | 1x TSLB* |

*+100 mM NaCl

Figure 14:
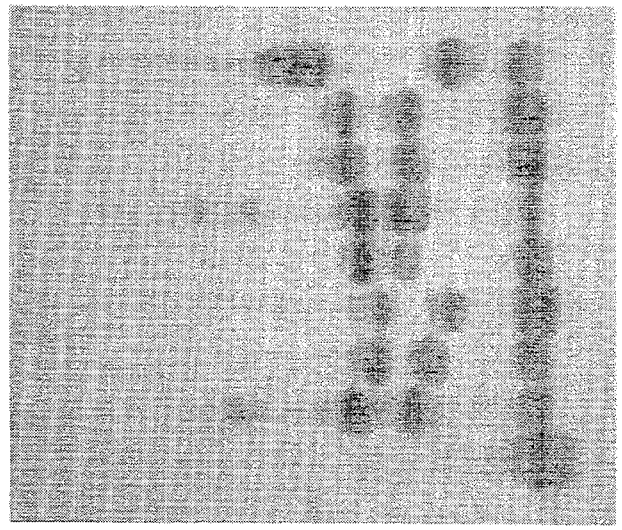
FIG. 14 is a photograph of an autoradiogram showing the relative cutting efficiencies of various remote cutting restriction enzymes with respect to the polysite DNA.

All eight of the reactions were incubated at 37° C. for 4 hours. Following incubation, one-half of each of the reactions was mixed with an equal volume of EDTA/dye reagent, heated at 90° C. for three minutes to quench the reaction, and then run on a 10% denaturing polyacrylamide gel using standard techniques known in the art and visualized by autoradiography. As shown in FIG. 14, while all of the remote cutters cleaved the modified polysite DNA, Fok I demonstrated the highest cutting efficiency in this system.

EXAMPLE 4

Figure 15:
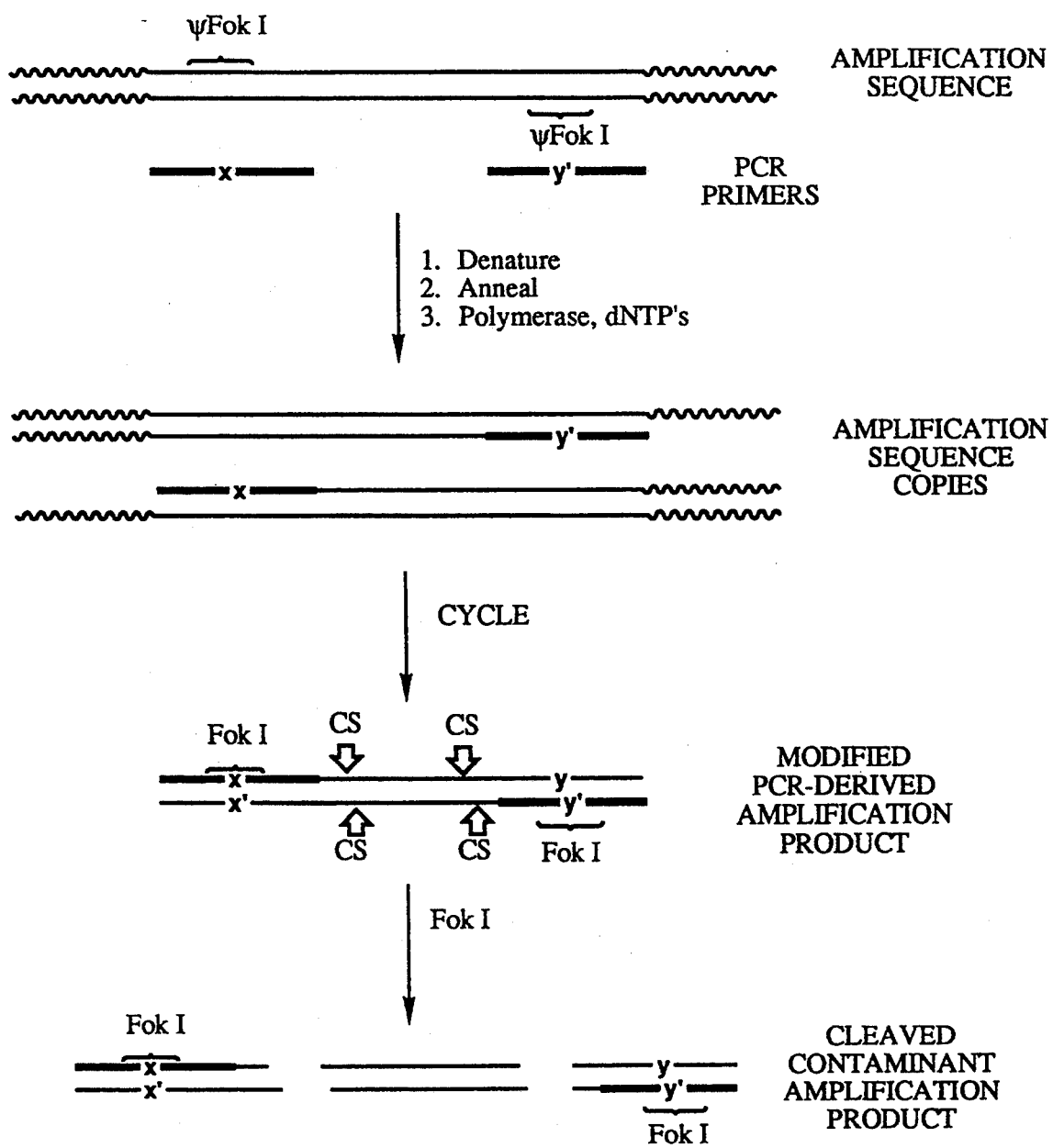
FIG. 15 is a diagram showing double restriction site modification of a PCR-derived amplification product and subsequent cleavage of the modified amplification product with a remote cutting restriction enzyme.

Double Remote Restriction Site Modification of PCR-derived Amplification Products Based on the results of the remote cutting enzyme evaluation from Example 3, a further example was designed to demonstrate the use of Fok I as a remote cutting restriction enzyme modification in a PCR type of amplification procedure. Two Fok I remote cutting restriction enzyme modification sites were introduced into PCR-derived amplification product as illustrated in FIG. 15. These modification sites were incorporated into the amplification product by using two appropriately modified PCR primers, each of which contained a single base mismatch with respect to a preferred pseudo Fok I restriction site located within the amplification sequence. Unlike a non-remote cutter site, incorporation of the remote cutting restriction enzyme recognition site into the modified amplification primer results in modified amplification product which contains the Fok I cleavage sites in the extended portion of the amplification product, even though the corresponding recognition sites lie within the primer-derived portion. Consequently, treatment of this modified amplification product with Fok I restriction enzyme results in cleaved products (as shown in FIG. 15) which are are not susceptible to the partial priming phenomenon described earlier.

Figure 16:
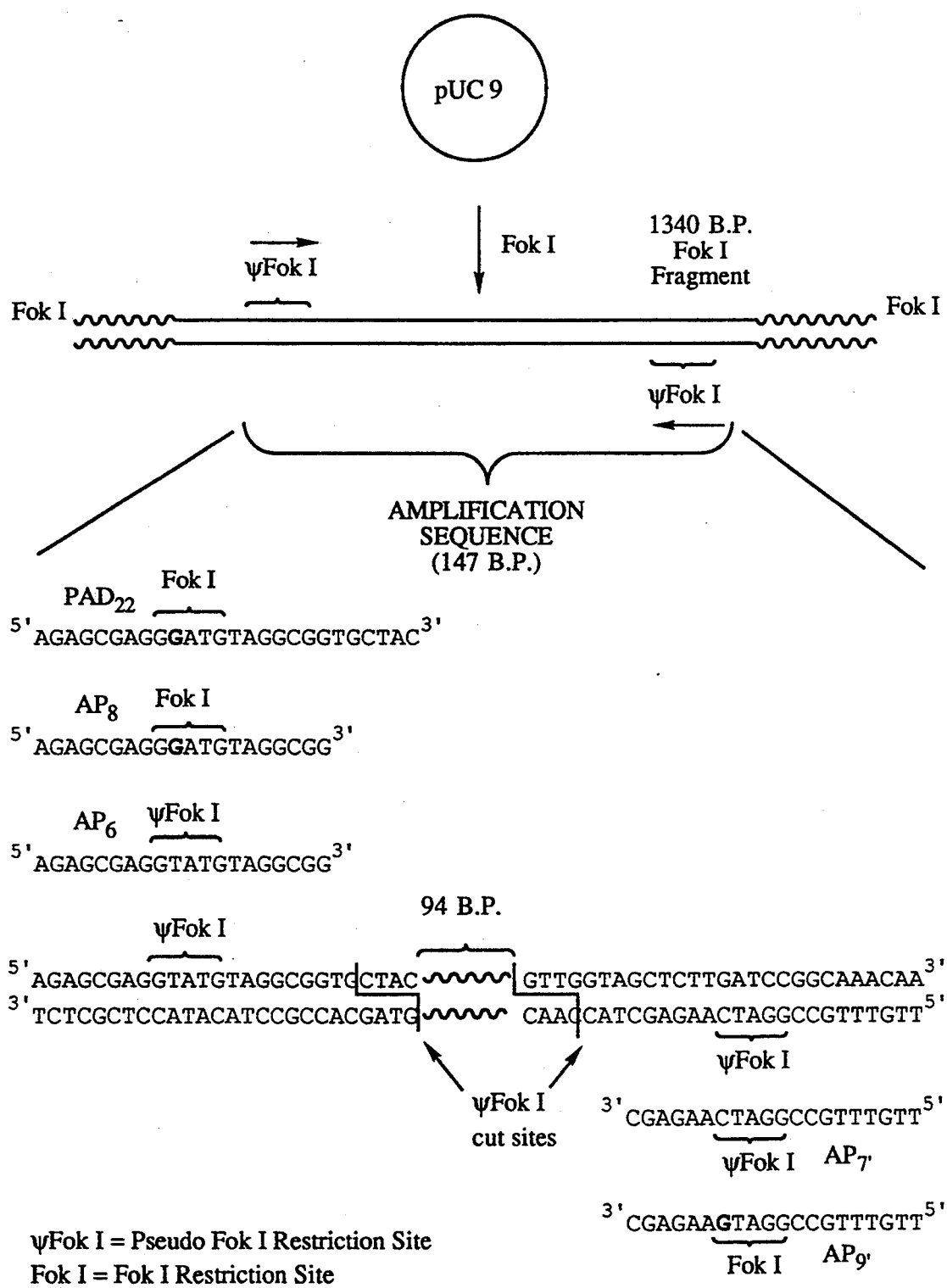
FIG. 16 shows a 147 base pair amplification sequence (contained in pUC 9), corresponding modified and unmodified PCR amplification primers, and a detection primer from Example 4.

A 147 base pair sequence contained within pUC 9 was selected as the amplification sequence for this example. The selected 147 base pair region is shown in FIG. 16, along with the sequences of native amplification primers AP$_6$ and AP$_7$' (containing no mismatches with respect to the target) single mismatched amplification primers AP$_8$ and AP$_9$' (to incorporate Fok I restriction enzyme recognition sites into amplification product) and PAD$_{22}$, a detection primer.

A. Preparation of pUC 9 Target for Amplification

The 2707 base pair pUC 9 plasmid was used as a source of target DNA for this example. The pUC 9 target DNA was prepared for amplification by cutting the circular plasmid with Fok I restriction endonuclease to achieve a linear sequence suitable for amplification. It was convenient to use the Fok I restriction enzyme, because it is the same enzyme which had already been selected for destruction of the appropriately modified amplification product. It is possible, however, to use other restriction enzymes to linearize or fragment the plasmid, provided an appropriate restriction site is located within the plasmid. The pUC 9 plasmid contains five Fok I recognition sites, with amplification sequence being contained within the largest (1340 base pair) Fok I fragment from the linearization treatment.

It should be noted, that where amplification cycle temperatures remain below about 95° C. it will ordinarily be necessary to fragment or linearize the plasmid, chromosome, or other target in a test sample to facilitate complete denaturation during the first cycle of amplification. Where amplification cycle temperatures exceed about 95° C. linearization and/or fragmentation will necessarily occur during amplification.

The following reagents were used:

Plasmid DNA, pUC 9, at a concentration of 0.45 μg/μl was obtained from Bethesda Research Laboratories (Gaithersburg, Md.).

Reaction Buffer was obtained by a 1/10 dilution of the [10×] reaction buffer supplied in the GeneAmp ™ DNA Amplification Reagent Kit from Perkin-Elmer/-Cetus (Norwalk, Conn.). The [10×] reaction buffer contains 100 mM Tris.HCl, 500 mM KCl, 15 mM $MgCl_2$ and 0.1% (w/v) gelatin. The Reaction Buffer thus obtained for use in this experiment was a [1×] Reaction Buffer.

Fok I restriction endonuclease at a concentration of 4 units/μl was obtained from New England Biolabs, Inc. (Beverly, Mass.).

The plasmid DNA was cut in the [1×] Reaction Buffer by adding 2 μl (0.9 μg) of pUC 9 DNA and 2 μl (8 units) of Fok I restriction endonuclease to 50 μl of the 1× Reaction Buffer. The resulting reaction mixture was allowed to incubate at 37° C. for 45 minutes, with any remaining enzyme activity being destroyed by heating at 90° C. for 10 minutes following the 45 minute incubation period. The concentration of target sequence in this reaction mixture was calculated at 9.25 femtomoles/μl.

B. PCR Amplification/Detection Using Native Amplification Primers vs. Modified Amplification Primers In order to determine if the single base mismatches contained within modified PCR primers would perform suitably in a PCR type of amplification procedure, side-by-side amplifications were performed using either native amplification primers ($AP_6$ and $AP_7'$, having complete complementarity with the amplification sequence) or modified amplification primers ($AP_8$ and $AP_9'$, having substantial complementarity with the amplification sequence). The side-by-side amplification reaction mixtures were cycled 20 times, with the products being subsequently visualized using the $PAD_{22}$ detection primer.

The following reagents used in this example were obtained as part of a Perkin-Elmer/Cetus GeneAmp ™ DNA Amplification Reagent Kit: 10 mM dNTP's (dATP, dCTP, dGTP, dTTP), [10×] Reaction Buffer (described in Example 4.A., above), and AmpliTaq ™ DNA Polymerase (5 units/μl).

Loading Buffer was the same as described in Example 2.B.

Detection primer $PAD_{22}$ was labeled on its 5'-end with $^{32}P$ to a specific activity of approximately 7000 Ci/mmole, as described in Example 2.C.

Target pUC 9 DNA was prepared by dilution of the Fok I-cut plasmid (from Example 4.A.) into TE (10 mM Tris, pH 8.0, 0.1 mM EDTA) until the desired concentration was achieved.

All amplification reactions were run in 0.5 μl Eppendorf ® tubes in a total volume of 50 μl of the 1× Reaction Buffer, which also contained the dNTP's at a concentration of 200 μM and 2.5 units of AmpliTaq ™ DNA polymerase. In addition to the above, the reactions also contained:

| | Amplification Primers | pUC 9 Target |
|---|---|---|
| Reaction 1: | 25 pmole each $AP_8$ and $AP_9'$ | 100 amole |
| Reaction 2: | 25 pmole each $AP_8$ and $AP_9'$ | 0.0 amole |
| Reaction 3: | 25 pmole each $AP_6$ and $AP_7'$ | 100 amole |
| Reaction 4: | 25 pmole each $AP_6$ and $AP_7'$ | 0.0 amole |

Two drops of mineral oil were added to each tube to prevent evaporation during amplification. The reactions were cycled 20 times in a Perkin-Elmer/Cetus Thermocycler by heating to 90° C. for 2 minutes, followed by 5 minutes at 50° C. for each cycle.

The amplification products were selectively visualized using the following polymerase-associated detection system (PAD). In this process, a labeled PAD primer is allowed to hybridize to the resulting amplification product in the presence of an excess of DNPs and a polymerase to generate a labeled extension (detection) product. This labeled detection product is then separated from excess labeled PAD primer on PAGE, and subsequently visualized by autoradiography. Because the PAD primer must compete with excess amplification primer for hybridization to amplification product, the PAD primer is designed to be longer (i.e., have a higher $T_m$) than the amplification primer. Thus, the reaction temperature can be adjusted to favor hybridization of the PAD primer.

To one tenth (5 μl) of each reaction mixture was added 1 μl of a solution containing 200 femtomoles of $^{32}P$-labeled detection primer ($PAD_{22}$) and 0.25 units of AmpliTaq ™ polymerase. The PAD primer was annealed and extended by heating the reactions to 90° C. for 5 minutes followed by 65° C. for 10 minutes. After cooling to room temperature, the reactions were quenched by the addition of 15 μl of loading buffer followed by heating to 90° C. for 5 minutes. The reactions were run along with a Hpa II-cut pBR 322 $^{32}P$-labeled marker on a 10% denaturing polyacrylamide gel using standard techniques, and visualized by autoradiography.

Figure 17:
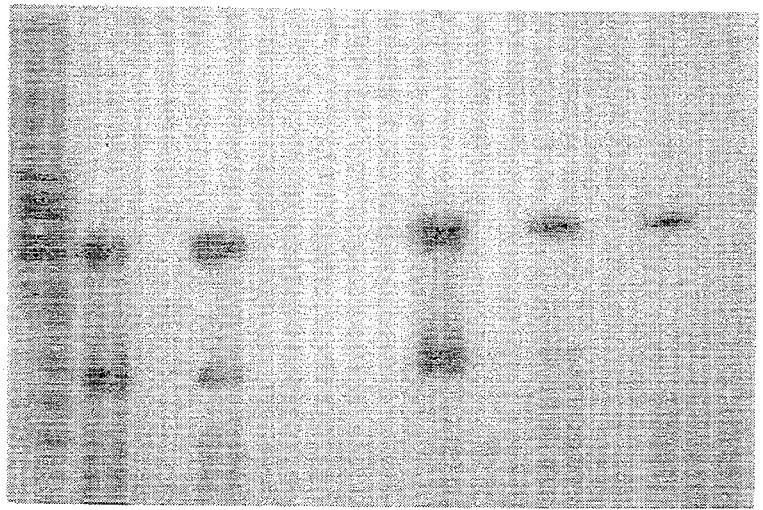
FIG. 17 is a photograph of an autoradiogram showing the relative efficiencies of PCR amplification using modified and unmodified primers, as well as the inability of the treated modified amplification product to serve as template in subsequent amplifications, as demonstrated in Example 4.B. and 4.C.

The relative intensities of the 147 base pair PAD products for each of the reaction mixtures are shown FIG. 17. The modified amplification primers, containing the single base mismatch at the pseudo restriction site of the amplification sequence, amplified with nearly the same efficiency as the native primers. (Compare the results from the Reaction 1 lane with the Reaction 3 lane.) The results from the zero controls (Reaction 2 and Reaction 4) demonstrate that no perceptible accumulation of product occurs from cycling in the absence of target.

C. Destruction of Modified PCR-derived Amplification Product

The same four reaction mixtures from Example 4.B. were treated with either active Fok I restriction endonuclease or heat inactivated Fok I (control), and then subjected to PAD detection to evaluate relative cutting efficiencies.

Fok I restriction endonuclease was used to destroy modified PCR-derived amplification product. All other reagents used in this example were obtained as part of the Perkin-Elmer/Cetus GeneAmp ™ DNA Amplification Reagent Kit as described in Example 4.B.

Heat inactivated Fok I restriction endonuclease (ΔFok I) was prepared by heating the concentrated stock of enzyme to 90° C. for 10 minutes. The resulting ΔFok I was confirmed to be inactive by its observed inability to cut plasmid pUC 9 DNA.

A 25 μl aliquot of the 1× Reaction Buffer was added to one-tenth (5 μl) of each Amplification Reaction (1, 2, 3, and 4) from Example 4.B, along with either 2 μl (8 units) of active Fok I (Reactions 1A, 2A, 3A, and 4A, respectively) or 2 μl of ΔFok I (Reactions 1Δ, 2Δ, 3Δ, and 4Δ, respectively). These reaction mixtures were allowed to incubate for 16 hours at 37° C. followed by 90° C. for 5 minutes.

The cutting efficiency of the Fok I and ΔFok I enzymes on the PCR-derived amplification product was evaluated using PAD detection. Following restriction enzyme treatment, a 15 μl aliquot was removed from each of the reaction mixtures and then added to 10.5 μl of a solution which was adjusted to be 0.95× in Reaction Buffer and contained 200 femtomoles of $^{32}$P-PAD$_{22}$ (specific activity of 7000 Ci/mmole), 2.5 units of AmpliTaq ™ DNA polymerase, and was 952 μM in each dNTP (final concentration of 392 μM). These reaction mixtures were then heated to 90° C. for 5 minutes followed by 65° C. for 10 minutes, in order to complete the extension reaction. The reactions were quenched by adding 25 μl of loading buffer, followed by heating to 90° C. for 5 minutes. Samples from the quenched reaction mixtures were run on 10% polyacrylamide gel electrophoresis (PAGE), and the products were visualized by autoradiography. The film was over-exposed during the autoradiography step in order to reveal the presence of cleavage products in even trace amounts.

Figure 18:
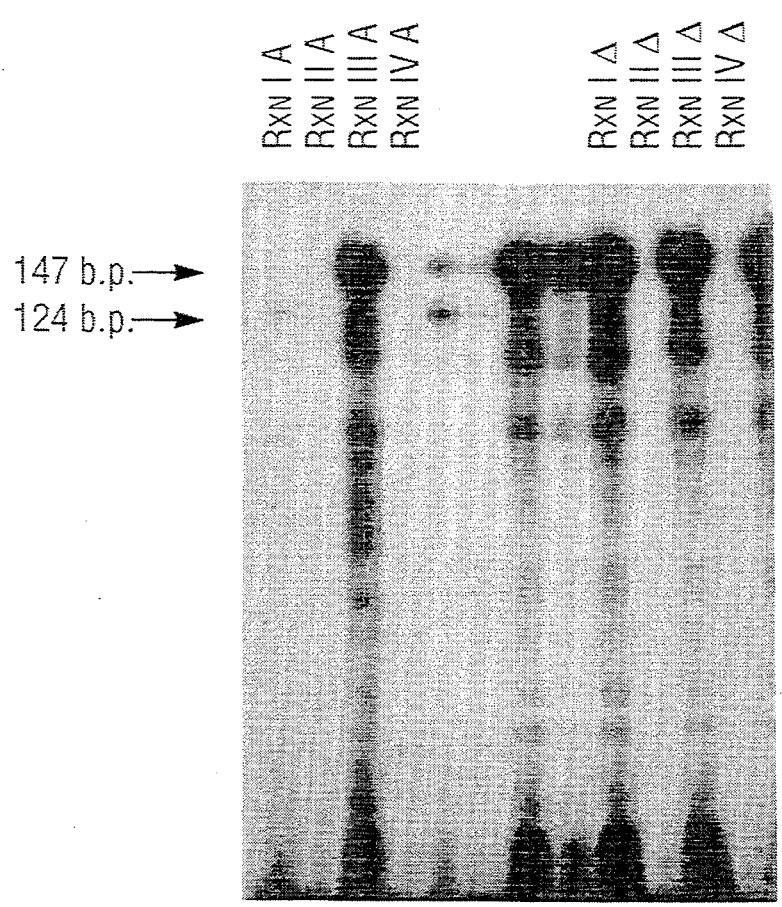
FIG. 18 is a photograph of an autoradiogram showing the effective destruction of a modified PCR-derived amplification product by treatment with the corresponding cutting agent, as demonstrated in Example 4.C.

As shown in FIG. 18, the modified amplification product resulting from the use of the single base mismatched modified amplification primers (containing Fok I sites) was completely destroyed by treatment with active Fok I enzyme (Reaction 1A). In contrast, amplification product formed with native primers was unaffected following exposure to the same active Fok I enzyme (Reaction 3A), as indicated by the strong PAD signal which appears at 147 base pairs on the autoradiogram. As expected, neither the modified nor the unmodified amplification product was affected by treatment with heat inactivated Fok I enzyme (Reactions 1Δ and 3Δ, respectively). The zero target controls (Reactions 2A, 4A, 2Δ, and 4Δ) did not show any products at 147 base pairs on the autoradiogram, confirming that all observed 147 base pair signals are indeed derived from amplification products.

Figure 19:
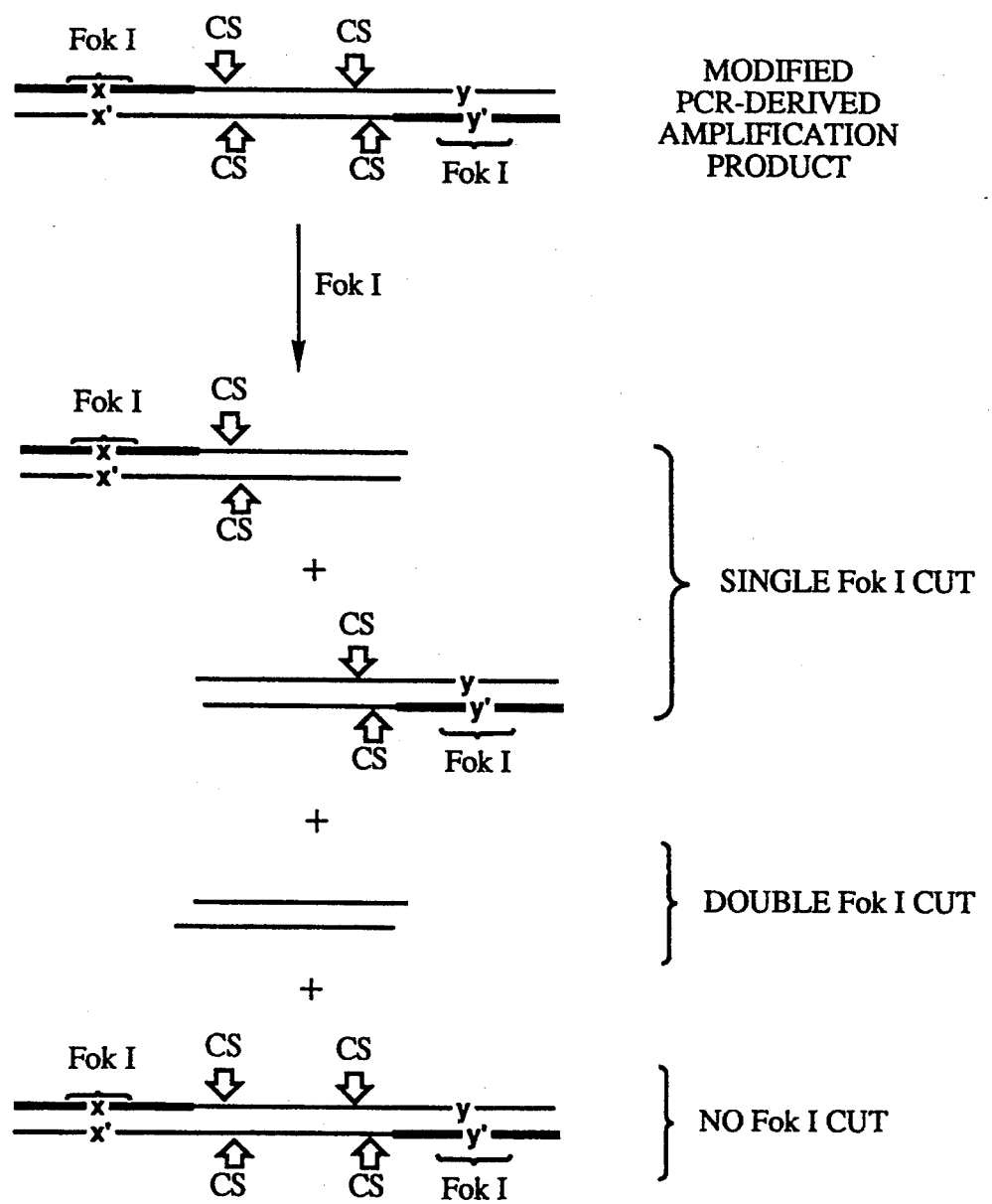
FIG. 19 is a diagram showing the products resulting from single and double cuts on a PCR amplification product containing two remote cutting restriction site modifications.

A slight signal was evident in the PAD detection reaction of Reaction 1A at about 127 base pairs. This errant signal was determined to arise from the PAD primer extending on a modified amplification product template that had been cut at only one of the two available Fok I sites as illustrated in FIG. 19. As shown in FIG. 19, there are two possible products that can result from single Fok I cutting, of which only one will respond to the PAD detection step, producing a 127 base pair product. It is important to note that neither of these partially cut modified amplification products is complementary to both of the modified amplification primers which is required for participation as a template in subsequent amplification procedures.

D. PCR Amplification of Fok I-Treated Amplification Products

In order to further examine the degree of cleavage in the reactions from Example 4.C., the same reaction mixtures were diluted and subjected to a second round of 20 cycles of PCR amplification with modified amplification primers AP$_8$ and AP$_9$', as previously described in Example 4.B. The resulting amplification products were then subjected to PAD detection, as described in Example 4.C. In the case of these "re-amplified" samples, even trace amounts of uncut amplification product were expected to be amplified to a detectable level, just as carryover contaminant product would be expected to produce a detectable signal in a clinical setting. All of the reagents for the reamplification and subsequent detection procedures were as previously described.

Each cleavage reaction from Example 4.C. was serially diluted in TE by a factor of 1/100,000. Because the cleavage reactions themselves effectively resulted in a 1/6 dilution of the original amplification reaction mixtures, the 1/100,000 dilution represents a total dilution of 1/600,000 with respect to the original amplification reaction mixtures. Further, since only 5 μl of the diluted samples were re-amplified, compared with the original volume of 50 μl of amplification reaction mixtures, the re-amplification represents only 1/6,000,000th of the total number of amplification products (both modified and unmodified) which were synthesized in situ as a consequence of the original PCR amplification of Example 4.B. This 1/6,000,000 figure is representative of the level of carryover contamination expected in a typical clinical laboratory setting.

Five microliters of each of the final dilutions (1/600,000) of the cleavage reaction mixtures were added to 45 μl of a solution which was adjusted such that the final solution, containing the 5 μl of diluted sample, was 1× in Reaction Buffer, 200 μM in each dNTP, and contained 25 picomoles of each amplification primer (AP$_8$ and AP$_9$'), and 2.5 units of AmpliTaq ™ polymerase. The reaction mixtures resulting from Reactions 1A, 2A, 3A, 4A, 1Δ, 2Δ, 3Δ, and 4Δ were designated as Reactions 1A+, 2A+, 3A+, 4A+, 1Δ+, 2Δ+, 3Δ+, and 4Δ+, respectively (where "+" indicates that the reactions were re-amplified with a second 20 cycles of PCR amplification). Two drops of mineral oil were added to each reaction mixture, after which the 0.5 ml Eppendorf® tubes were sealed and cycled 20 times in a Perkin-Elmer/Cetus Thermocycler by heating to 90° C. for 2 minutes followed by 50° C. for 5 minutes for each cycle.

A 1 μl aliquot of a solution containing 200 femtomoles of $^{32}$P-labeled detection primer (PAD$_{22}$) and 0.25 units of AmpliTaq ™ polymerase was added to one-tenth (5 μl) of each re-amplified reaction mixture. The PAD detection reaction was run by heating the reaction mixtures to 90° C. for 5 minutes, followed by 65° C. for 10 minutes. The reaction products were quenched with 15 μl of loading buffer and heated to 90° C. for 5 minutes, before running on denaturing 10% PAGE, along with a Hpa II-cut pBR 322 $^{32}$P-labeled marker, and visualized by autoradiography. A photograph of the results is shown in FIG. 17. (It should be noted that this gel and autoradiogram also contain the data from Reactions 1, 2, 3, and 4 from Example 4.B., above.)

Reactions 1Δ+ and 3Δ+ displayed the types of signals that would be expected to result from PCR amplification of samples which had been contaminated with 1/6,000,000th of the products from Reactions 1 and 3, respectively. These results illustrate a typical false positive resulting from this level of contamination in a 20-cycle PCR type of amplification. In contrast, amplification of sample contaminated with modified amplification product which had previously been treated with active Fok I restriction enzyme (Reaction 1A+)

yielded no detectable 147-mer product, in other words, no false positive. Treatment of the unmodified amplification product with the Fok I restriction enzyme (reaction 3A+), resulted in a signal of equal intensity compared with treatment of this same unmodified amplification product with heat inactivated Fok I enzyme (Reaction 3A+). This demonstrates selective destruction of the modified amplification product will be by treatment with active Fok I restriction endonuclease in the presence of native target sequence, remains unaffected by this treatment. The zero target amplifications (Reactions 2A+, 2Δ+, 4A+, and 4Δ+) showed no detection products, confirming that the 147-mer products were indeed derived from amplification product templates, and not spuriously formed.

EXAMPLE 5

Double Remote Restriction Site Modification of PCR-derived Amplification Products: Cutting After Contamination While Example 4 demonstrates the successful post-amplification treatment of a previously amplified test sample to remove carryover contamination, it would, as previously noted, be more effective in a laboratory environment to "pre-treat" new test samples with the appropriate cutting agent immediately prior to amplification of the new test sample. In this way, any contaminant amplification product would be destroyed in new samples by a pre-incubation step which would include addition of the cutting agent (e.g., Fok I) in a sealed tube, with all amplification reagents present, just before amplification is commenced.

A potential concern with regard to the use of pre-treatment contamination control is presented by the expected very low initial concentration of contaminant amplification product in the new test samples. This concern arises, because of the observed loss of catalytic activity of certain cutting agents at these types of low substrate concentrations. Therefore the effectiveness of the cutting agent at destroying modified amplification product in new test samples could severely minimize the effectiveness of pre-treatment contamination control. (Example 4 shows that the cutting agent is very effective when the modified amplification product is treated with cutting agent immediately after amplification where the modified product is at a relatively high concentration.)

Figure 20:
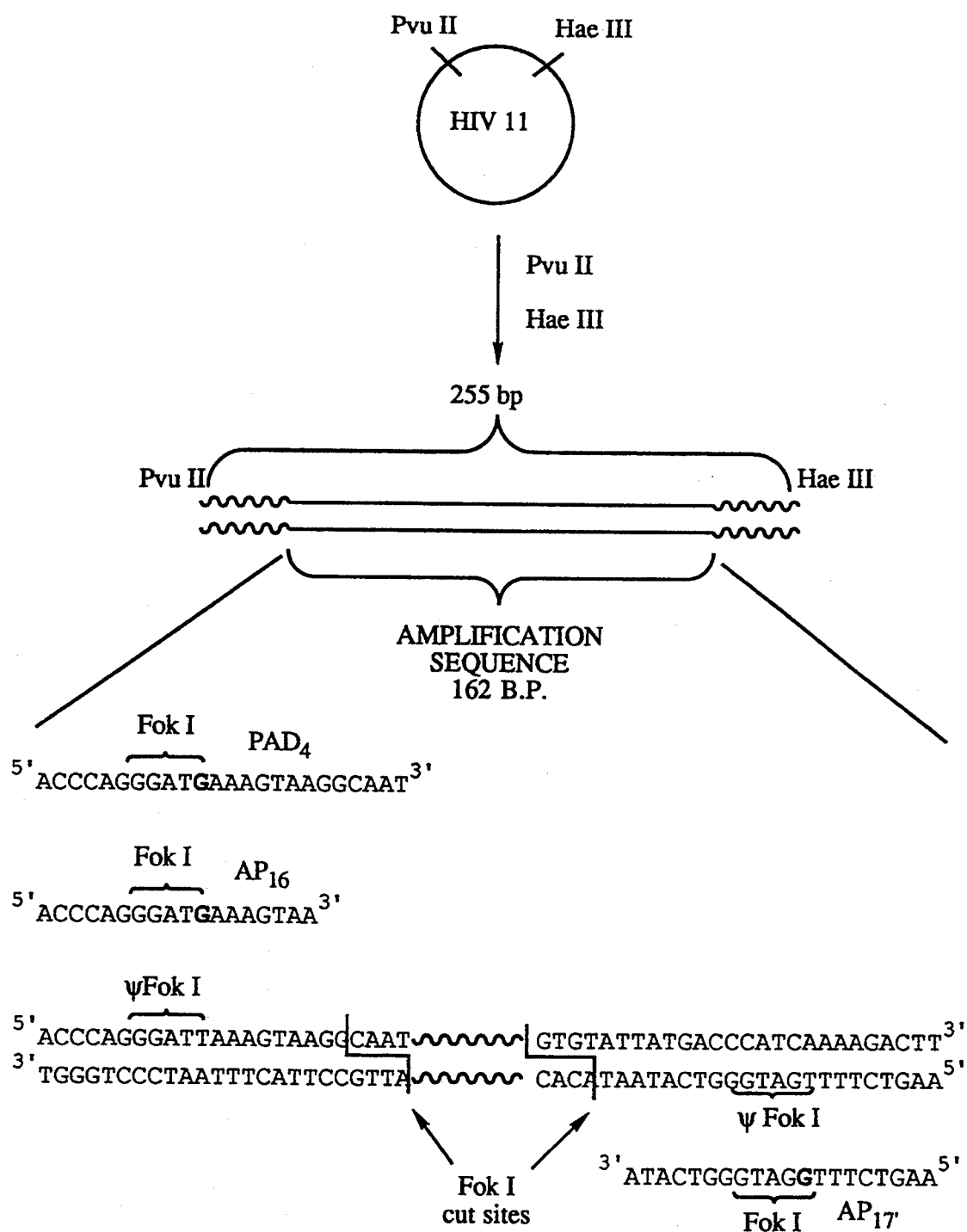
FIG. 20 shows a 162 base pair HIV amplification sequence, corresponding modified amplification primers and a detection primer from Example 5.

In order to test whether contamination can be controlled in this manner, a 162 base pair portion of the HIV pol gene was amplified using modified amplification primers $AP_{16}$ and $AP_{17}'$ to incorporate Fok I restriction sites into the amplification products. The product was quantitated by comparison of the PAD detection signal from extension of detection primer $PAD_4$ on the resulting products to that obtained from standards. The oligonucleotide sequences used in this study are shown in FIG. 20. This modified amplification product was then diluted and added to subsequent amplification reactions containing native target in order to simulate a controlled contamination experiment. The resulting contaminated samples were then treated with either active cutting agent (Fok I) or inaction cutting agent (ΔFok I) prior to amplification. Comparison of the resulting signals provided an indication of the efficiency of destruction of the contaminating product by treatment with the cutting agent.

A. PCR Amplification of HIV with Modified Amplification Primers and Quantitative Detection of the Modified Product The nucleic acid used for target and standards in the following experiment was a 10.0 kb pBR 322 clone containing approximately 6 kb of HIV (BH10 isolate; Gallo et al, *Nature*, 313, 277–284 (1985)). The clone was linearized for amplification by cutting with BamH I. The same clone was used to generate standards for the quantitation of product in the detection step by cutting with Pvu II and Hae III to produce a 255 base pair fragment containing the 162 base pair fragment to be amplified. The detection primer $PAD_4$ should extend on this fragment to product a 192 base product. The yield of PCR product can then be estimated by comparing the resulting 162-mer detection product to the 192-mer product resulting from known amounts of the standard.

The following reagents were obtained as part of a Perkin-Elmer/Cetus (Norwalk, Connecticut) GeneAmp ™ DNA Amplification Reagent Kit: 10 mM dNTPs (dATP, dCTP, dGTP, and dTTP), and [10×] Reaction Buffer, as described in Example 4.A.

AmpliTaq ™ DNA polymerase was obtained from PerkinElmer/Cetus at a concentration of 8 units/μl.

Thermophilic DNA Polymerase was obtained as a gift from Molecular Biology Resources, Inc. (Milwaukee, Wis.) at a concentration of 3 units/μl.

Restriction Endonucleases BamH I (25 units/μl), Pvu II (50 units/μl), and Hae III (10 units/μl), and their respective 10× cutting buffers were obtained from New England Biolabs, Inc. (Beverly, Mass.). The [10×] BamH I buffer was 1500 mM NaCl, 60 mM Tris (pH 7.9), 60 mM $MgCl_2$, 60 mM β-mercaptoethanol, and contained BSA at a concentration of 100 μg/ml. The [10×] Hae III buffer was 200 mM Tris (pH 7.9), 100 mM Mg Acetate, 500 mM K Acetate, and 10 mM DTT. The [10×] Pvu II buffer was 100 mM Tris (pH 7.9), 100 mM $MgCl_2$, 500 mM NaCl, and 10 mM DTT.

Oligonucleotide Sequences $AP_{16}$, $AP_{17}'$, and $PAD_4$ were synthesized and purified as described in Example 1.

Oligonucleotide $PAD_4$ was labeled on the 5'-end with $^{32}P$ to a specific activity of approximately 7000 Ci/m-mole, as described in Example 2.C.

Human Placental DNA (HP-DNA, Sigma Chemical Company, St. Louis, Mo.) was used as carrier DNA and was treated by heating a solution at a concentration of 10 mg/ml in 5 mM $MgCl_2$ for 10 minutes at 90° C.

Target sequence was prepared by linearizing an HIV clone in pBR 322 (HIV 11) containing approximately 5700 base pairs of HIV sequence with BamH I. The clone (0.026 μg) was incubated with 25 units of BamH I in 20 μl of 1× BamH I buffer for 4 hours at 37° C. After cutting, the target was diluted such that the desired number of target molecules were contained in 5 μl of TE with HP-DNA present at a concentration of 1 μg/μl.

Standard used to quantitate the amplification products was prepared as follows: Two μg of the same clone used to prepare target was incubated in 100 μl of 1× Pvu II cutting buffer containing 250 units of Pvu II for 1 hour at 37° C. The solution was adjusted to 0.3 μM in NaCl using 5.0 M NaCl and 3 volumes of ethanol was added to precipitate the DNA. After spinning at 14,000×g for 30 minutes, the DNA pellet was isolated by decanting the supernatant and drying the DNA under vacuum. The pelleted DNA was then cut with 50 units of Hae III restriction enzyme in 100 μl of 1× Hae III restriction buffer by incubating for 1 hour at 37° C. Residual enzyme activity was destroyed by heating the reaction to 90° C. for 5 minutes. The resulting 255 base pair restriction fragment, containing the 162 base pair amplification region, should hybridize with the detection primer $PAD_4$ and extend in the presence of dNTPS and polymerase to form a 192 base product that can be used to quantitate the 162 base amplification extension product.

All amplification reactions were run in 0.5 ml Eppendorf® tubes in a total volume of 50 μl of 1× Reaction Buffer, which also contained each dNTP at a concentration of 200 μM, 25 pmoles of each amplification primer ($AP_{16}$ and $AP_{17}'$), 5.0 μg of HP-DNA, and 2.5 units of AmpliTaq ™ DNA polymerase. In addition to the above, the reactions also contained:
Reaction 1: 25,000 molecules of target
Reaction 2: 1,000 molecules of target
Reaction 3: 0.0 molecules of target Two drops of mineral oil were added to each tube to prevent evaporation during amplification. The reactions were cycled 25 times in a Perkin-Elmer/Cetus Thermocycler by heating to 90° C. for 2 minutes, followed by 5 minutes at 50° C. for each cycle. The amplification products along with standards were selectively visualized using the $PAD_4$ detection primer, as described below.

The detection reactions were run in a total volume of 30 μl of 1× Reaction Buffer which also contained each dNTP at a concentration of 333 μM, 200 femtomoles of $PAD_4$ (7000 Ci/mmole), and 0.6 units of Thermophilic polymerase (MBR). In addition to the above, the detection reactions also contained:

| Reaction | Pvu II/Hae III Cut Standard | Amplification Reaction |
| --- | --- | --- |
| 1S | 50 femtomoles | |
| 2S | 40 femtomoles | |
| 3S | 30 femtomoles | |
| 4S | 20 femtomoles | |
| 5S | 10 femtomoles | |
| 6S | 2.0 femtomoles | |
| 1A | | 5.0 μl of Reaction 1 |
| 2A | | 5.0 μl of Reaction 2 |
| 3A | | 5.0 μl of Reaction 3 |

Figure 21:
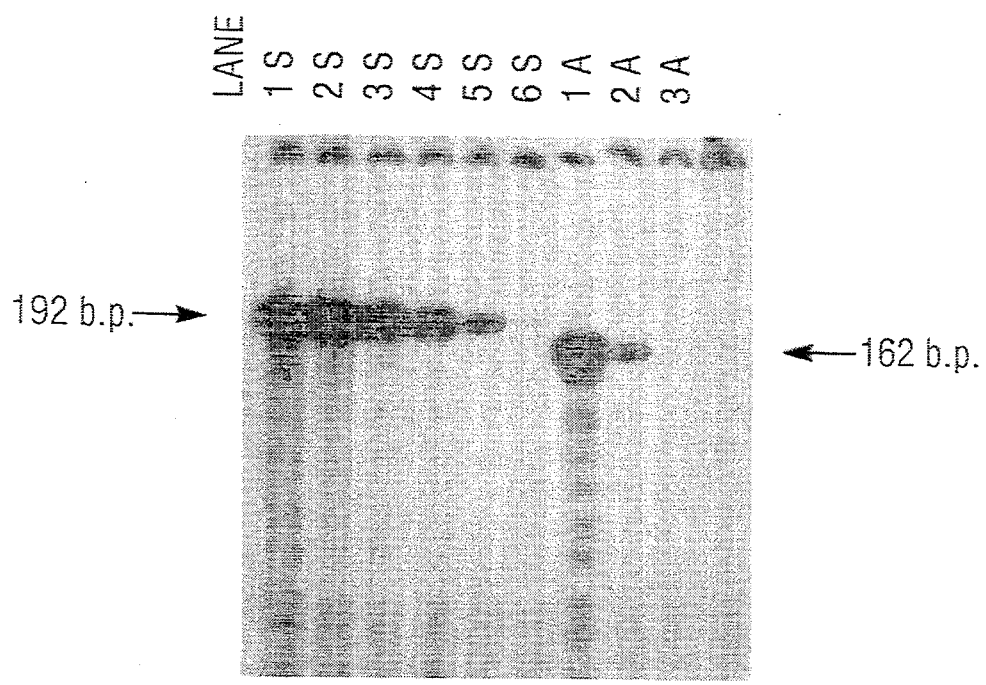
FIG. 21 is a photograph of an autoradiogram showing the formation and quantitation of PCR-derived modified amplification product, as demonstrated in Example 5.A.

The detection reactions were run by heating the tubes to 90° C. for 5 minutes followed by incubation at 60° C. for 10 minutes. The reactions were quenched by adding 30 B1 of loading buffer and heating to 90° C. for 3 minutes followed by cooling to room temperature. The products were analyzed by running the samples on 15% denaturing PAGE followed by autoradiography. As shown in the photograph of the autoradiogram in FIG. 21, the standards (Lanes 1S-6S) produce a detection product of slightly slower mobility than the detection product from the amplification reactions (Lanes 1A-3A). This is consistent with the calculated sizes of 192 and 162 base pairs, respectively.

The amplification reactions show a linear response to the amount of starting target and the zero target reaction (Lane 3A) does not show any sign of product. Reaction 2 (Lane 2A) can be estimated to contain approximately 10 femtomoles/5 μl of reaction by comparison to the signal produced from the 10 femtomole standard (Reaction 5S). The modified reaction product from this amplification was used in the controlled contamination experiments detailed below.

B. PCR Amplification of HIV in the Presence of Contamination with and without Cutting In this experiment, wild type target (1000 or 0 molecules) was contaminated with either 200,000, 20,000, or 0 molecules of modified amplification product from Reaction 2A. The reactions were then treated with either active cutting agent (Fok I) or inactive cutting agent (ΔFok I). After incubation with the cutting agent in closed reaction tubes for a predetermined time, the reactions were cycled to achieve amplification. The first PCR cycle temperature of 90° C. destroys any Fok I activity, such that the newly formed modified amplification products accumulate exponentially from the uncut wild type target molecules.

All reagents used in this example were the same as previously described in Example 5.A., with the exception of the following additional reagents. Fok I restriction endonuclease at a concentration of 4 units/μl was obtained from New England Biolabs, Inc. (Beverly, Mass.).

The inactive cutting agent, ΔFok I, was obtained by heating a portion of the Fok I enzyme in a boiling water bath for 10 minutes.

Loading Buffer was the same as described in Example 2.B.

Modified amplification product from Reaction 2A (starting concentration of 2 femtomoles/μl), used to contaminate the samples, was serially diluted into water to obtain the desired number of contaminating molecules for addition to the samples.

All of the reactions were run in 0.5 ml Eppendorf® tubes in a total volume of 50 μl of 1× Reaction Buffer, which also contained each dNTP at a concentration of 200 mM, 25 picomoles of each amplification primer ($AP_{16}$ and $AP_{17}'$), 5.0 μl of HP-DNA and 2.5 units of AmpliTaq ™ DNA polymerase. In addition to the above, the reactions also contained:

| Reaction | Target Molecules | Contamination Molecules | Cutting Agent |
| --- | --- | --- | --- |
| 1 | 1000 | 20,000 | Fok I |
| 2 | 1000 | 20,000 | Fok I |
| 3 | 0 | 20,000 | Fok I |
| 4 | 0 | 20,000 | Fok I |
| 5 | 1000 | 20,000 | ΔFok I |
| 6 | 1000 | 20,000 | ΔFok I |
| 7 | 0 | 20,000 | ΔFok I |
| 8 | 0 | 20,000 | ΔFok I |
| 9 | 1000 | 200,000 | Fok I |
| 10 | 1000 | 200,000 | Fok I |
| 11 | 0 | 200,000 | Fok I |
| 12 | 0 | 200,000 | Fok I |
| 13 | 1000 | 200,000 | ΔFok I |
| 14 | 1000 | 200,000 | ΔFok I |
| 15 | 0 | 200,000 | ΔFok I |
| 16 | 0 | 200,000 | ΔFok I |
| 17 | 1000 | 0 | None |
| 18 | 1000 | 0 | None |
| 19 | 0 | 0 | None |
| 20 | 0 | 0 | None |

Reactions designated to include Fok I contained 8 units of the active enzyme. Reactions designated to include ΔFok I contained an equal amount of the heat inactivated form of the enzyme. Two drops of mineral oil were added to each tube to prevent evaporation during amplification. The reactions were placed in a Perkin-Elmer/Cetus thermocycler and heated at 37° C. for 60 minutes to complete the cutting reactions followed by 25 cycles of heating to 90° C. for 2 minutes and 50° C. for 5 minutes to complete the amplification reactions. The reaction products were detected by combining 5 μl of each reaction with 1 μl of a solution of $^{32}$P-labeled PAD$_4$ in TE (200 femtomoles, 7000 Ci/mmole), followed by heating to 90° C. for 5 minutes, then 60° C. for 10 minutes. After cooling to room temperature, 10 μl of loading buffer was added, and the reactions were heated to 90° C. for 3 minutes and again cooled to room temperature. The reactions were analyzed by running the samples on a 15% denaturing PAGE followed by autoradiography.

Figure 22:
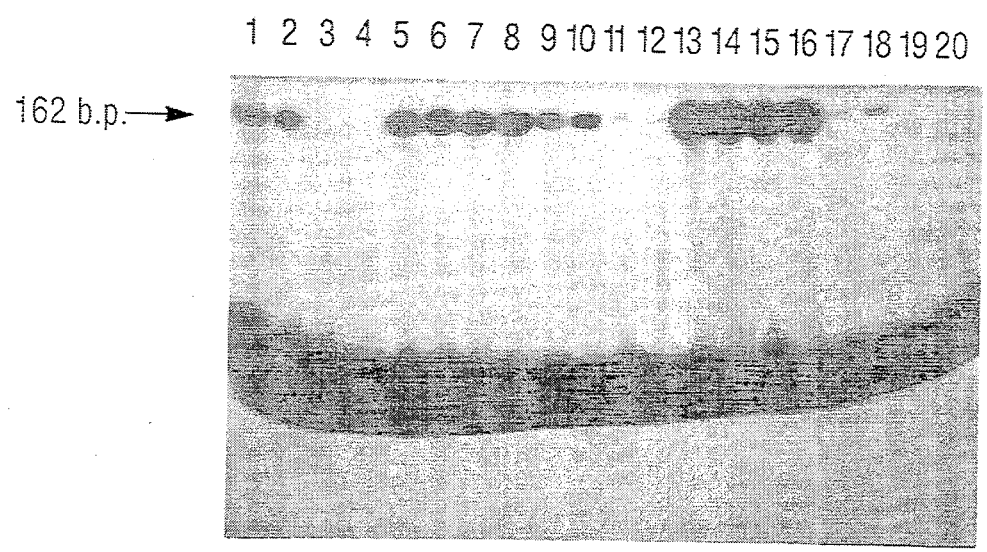
FIG. 22 is a photograph of an autoradiogram showing the effective "pre-amplification" destruction of carryover contamination in a PCR type of amplification procedure, as demonstrated in Example 5.B.

A photograph of the autoradiogram (FIG. 22) shows that contaminated samples that were treated with inactive cutting agent prior to amplification give strong false positives (162-ruer product) in the zero target lanes (reactions 7, 8, 15, and 16). This makes it impossible to see true positives (reactions 5, 6, 13, and 14) due to the large background signals. In contrast, the contaminated samples that were treated with active cutting agent prior to amplification show strong 1000 molecule controls (reactions, 1, 2, 9, and 10) relative to their respective zero molecule controls (Reactions 3, 4, 11, and 12). It is interesting to note that the signals resulting from 1000 molecules of target where Fok I was used to cut contamination (reactions 1, 2, 9, and 10) are much more pronounced than the signals resulting from 1000 molecules of target that were never contaminated or treated with Fok I (Reactions 17 and 18). We have no explanation for this phenomena of enhanced amplification signals in amplification reactions that contain Fok I, however, it has been observed routinely.

This mode of contamination control is especially attractive, because the amplification reactions never need to be opened after treatment with the cutting agent in order to begin the amplification reactions. This ensures that no untreated contamination can enter the reaction vessel prior to amplification to produce false positives.

EXAMPLE 6

Ribonucleotide Modification of PCR-derived Amplification Product: Chemical vs. Enzymatic Cleavage of Modified Amplification Product In this example, a single ribonucleotide substitution was made in each amplification primer in order to introduce a labile modification into each strand of the resulting PCR-derived amplification product. The labile bonds in the resulting amplification product were created by polymerase extension off of the modified amplification primers which contained the single ribonucleotide on their respective 3'-ends. This rendered the modified amplification product amenable to both enzymatic destruction (with RNAse A at lower temperatures) and chemical destruction (in the presence of a strong base at elevated temperatures).

A 75 base pair region of HIV was employed as the amplification sequence. This 75-mer target was amplified using two 15-mer amplification primers (AP$_{18}$ and AP$_{21}$') and a 26-mer detection primer (PAD$_5$), as shown in FIG. 23.

A. PCR Amplification of HIV with Modified Amplification Primers and Quantitative Detection of the Resulting Modified Amplification Product In this example, an HIV clone pBH10 (Hahn, et al, Nature, 312, 166 (1984)) was amplified using the modified amplification primers AP$_{18}$ and AP$_{21}$' containing a single ribonucleotide modification on their 3'-ends. The resulting modified amplification products were then quantitated by serial dilution and re-amplification concurrently with known amounts of wild type target standards. These quantitated modified amplification product samples were reserved for later use in subsequent experiments.

AmpliTaq ™ DNA Polymerase was obtained from Perkin-Elmer/Cetus at a concentration of 8 units/μl.

Deoxynucleoside-5'-triphosphates (dATP, dCTP, dGTP, and dTTP) were obtained as part of the PerkinElmer/Cetus GeneAmp ™ Amplification Reagent Kit at a concentration of 10 mM each.

Reaction Buffer [10×] contained 100 mM Tris (pH 8.3), 500 mM KCl, 30 mM MgCl$_2$, and gelatine (Difco Laboratories, Detroit, Mich.) at a concentration of 1 μg/ml.

Oligonucleotide sequences AP$_{18}$, AP$_{21}$' and PAD$_5$ were synthesized and purified as described in Example 1, with the exception that AP$_{18}$ was synthesized from a RNA support beginning with guanosine, and AP$_{21}$' was synthesized from a RNA support beginning with uracil. These RNA supports are commercially available from Glen Research Corporation (Herndon, Va.).

Detection oligonucleotide PAD$_5$ was labeled on the 5'-end with $^{32}$P to a specific activity of approximately 7000 Ci/mmole, as described in Example 2.C.

Human Placental DNA (HP-DNA, Sigma Chemical Company) was used as carrier DNA, and was treated by heating a solution at a concentration of 10 mg/ml in 10 mM MgCl$_2$ for 10 minutes in a boiling water bath.

Target HIV DNA was prepared by diluting an HIV clone pBH10 in TE to the desired molecule level and adding an equal volume of a solution of the HP-DNA in TE at a concentration of 2 μg/ml. The presence of HP-DNA prevents non-specific binding of low amounts of target DNA to the container.

All amplification reactions were run in 0.5 ml Eppendorf®reaction tubes in a total volume of 100 μl of 1× Reaction Buffer, which also contained each dNTP at a concentration of 100 μM, 50 picomoles of each amplification primer (AP$_{18}$ and AP$_{21}$'), 5.0 μg of HP-DNA, and 3.2 units of AmpliTaq ™ polymerase. In addition, each of the reaction vessels also contained:
Reaction 1–4: 1000 molecules of target
Reaction 5–6: 0 molecules of target Two drops of mineral oil were added to each tube to prevent evaporation during amplification. The reactions were cycled 30 times in a Perkin-Elmer/Cetus Thermocycler by heating to 95° C. for 30 seconds, followed by 50° C. for 5 minutes for each cycle.

After cycling was completed, Reactions 1–4 (1000 molecules of target) were combined, as were Reactions 5 and 6 (0 molecules of target) in order to provide homogeneous working stocks of both the modified amplification product and the corresponding zero molecule control. The combined Reactions 1–4 are referred to as Reaction 1K, while the combined controls, Reactions 5 and 6, are referred to as Reaction OK.

The amplification products were detected by combining 10 μl of either Reaction 1K or Reaction OK with 1 μl of $^{32}$P-labeled detection probe PAD$_5$ (7000 Ci/mmole, 100 femtomoles/μl) and heating to 95° C. for 2 minutes, followed by 60° C. for 10 minutes. After cooling to room temperature, 10 μl of loading buffer was added and the reactions heated to 90° C. for 3 minutes, followed again by cooling to room temperature. The reaction products were analyzed by running the samples on 10% denaturing PAGE, followed by autoradiography.

Figure 24:
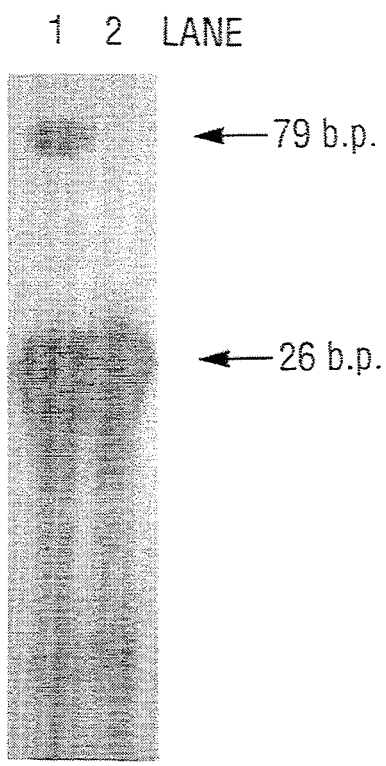
FIG. 24 is a photograph of an autoradiogram showing PCR amplification using PCR primers containing a single ribonucleotide substitution on their respective 3'-ends, as demonstrated in Example 6.A.

As shown in FIG. 24, there is a very strong detection signal (a 79-mer made up of a 75-mer plus an additional 4 adenosine residues on the PAD primer) from the 1000 molecule reactions (Reaction 1K in Lane 1), and no detectable signal from the 0 molecule reactions (Reaction 0K in Lane 2). This indicates that this type of modified primer is suitable for PCR type amplification procedures.

The amount of amplification product was estimated by running a PCR amplification on serial dilutions of Reaction 1K along with known amounts of wild type target.

All amplification reactions were run in 0.5 ml Eppendorf® tubes in a total volume of 50 μl of 1× Reaction Buffer, which also contained each dNTP at a concentration of 200 μM, 25 picomoles of each amplification primer (AP$_{18}$ and AP$_{21}$'), 5.0 μg of HP-DNA, and 3.2 units of AmpliTaq ™ DNA polymerase. In addition, each of the reactions also contained:

Reaction 7: 1000 molecules of target
Reaction 8: 1000 molecules of target
Reaction 9: 200 molecules of target
Reaction 10: 200 molecules of target
Reaction 11: 0 molecules of target
Reaction 12: 0 molecules of target
Reaction 13: 5 μl of a ⅓×10$^5$ dilution of Rxn 1K
Reaction 14: 5 μl of a ⅓×10$^5$ dilution of Rxn 1K
Reaction 15: 5 μl of a ⅓×10$^6$ dilution of Rxn 1K
Reaction 16: 5 μl of a ⅓×10$^6$ dilution of Rxn 1K
Reaction 17: 5 μl of a ⅓×10$^7$ dilution of Rxn 1K
Reaction 18: 5 μl of a ⅓×10$^7$ dilution of Rxn 1K Two drops of mineral oil were added to each tube to prevent evaporation during amplification. Each reaction tube was cycled 30 times in a Perkin-Elmer/Cetus Thermal Cycler by heating to 95° C. for 30 seconds followed by 50° C. for 5 minutes for each cycle to achieve amplification. The resulting amplification products were detected by combining 10 μl from each reaction tube with 1 μl of a solution of $^{32}$P-labeled oligonucleotide PAD$_5$ (7000 Ci/mmole, 100 femtomoles/μl) and heating to 95° C. for 2 minutes followed by 60° C. for 10 minutes. After cooling to room temperature, 10 μl of loading buffer was added to each reaction and the detection products denatured by heating to 90° C. for 3 minutes, followed by cooling to room temperature. The detection products were visualized by running the samples on 10% denaturing PAGE, followed by autoradiography.

Figure 25:
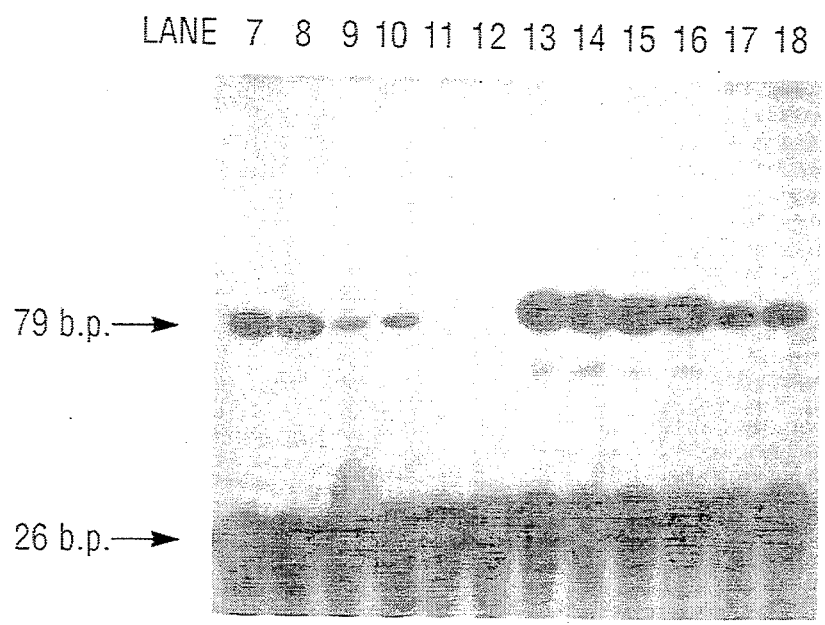
FIG. 25 is a photograph of an autoradiogram showing the quantitation of ribonucleotide modified PCR-derived amplification product by comparison to standards, as demonstrated in Example 6.A.

A photograph of the autoradiogram shown in FIG. 25 shows that the product yield from the ⅓×10$^7$ dilution of Reaction 1K (Lanes 17 and 18) gave a signal of equal intensity to the 1000 molecule wild type standard (Lanes 7 and 8). Thus, Reaction 1K contains 3×10$^{10}$ molecules of modified amplification product per 5 μl of reaction volume. This would correspond to an average cycle efficiency of 92% for the original amplification.

B. Cutting of Modified Amplification Product with RNAse A

In this experiment, the modified amplification product from Example 6.A. was subjected to RNAse A immediately prior to detection using oligonucleotide PAD$_5$. If the ribonucleotide is present in the amplification product, then one would expect to see a detection product which is 15 bases shorter than the full length product. Because RNAse A is specific for ribo-pyrimidines, only the lower strand should be cleaved in this reaction (i.e., the lower strand of the modified amplification product contains a single uracil ribonucleotide linkage, while the only ribonucleotide component of the upper strand is ribo-guanosine, a purine). Further, because the labeled detection primer hybridizes and extends off of the lower strand, the degree of cutting should be apparent by the presence of a shorter (64-ruer) detection product.

RNAse A was purchased from Sigma Chemical Company and dissolved in TE/150 mM NaCl at a concentration of 10 mg/ml. DNAse activity was destroyed by heating this solution for 15 minutes in a boiling water bath. A 1/200 dilution (50 μg/ml) of this stock into 150 mM NaCl was heated in a boiling water bath for an additional 15 minutes and cooled to room temperature for use in the following experiment.

The detection primer PAD$_5$ was the same as previously described in Example 6.A.

Reaction 1K and Reaction 0K from the previous experiment were used as a source of modified amplification product.

The cutting reactions were set up as follows:

| Reaction | Product | RNAse |
|---|---|---|
| 1 | 10 μl Reaction 1K | 1 μl |
| 2 | 10 μl Reaction 1K | 0 μl |
| 3 | 10 μl Reaction 0K | 1 μl |
| 4 | 10 μl Reaction 0K | 0 μl |

The cutting reactions were allowed to proceed for 2 hours at room temperature, and the resulting products were detected by adding 1 μl of $^{32}$P-labeled PAD$_5$(7000 Ci/mmole, 100 femtomoles/μl), followed by heating to 95° C. for 2 minutes and then 60° C. for 10 minutes. After cooling to room temperature, 10 μl of loading buffer was added, and the samples were denatured by heating to 90° c. for 3 minutes, and then cooling to room temperature. The reaction products were then analyzed by running the samples on denaturing 10% PAGE, followed by autoradiography.

Figure 26:
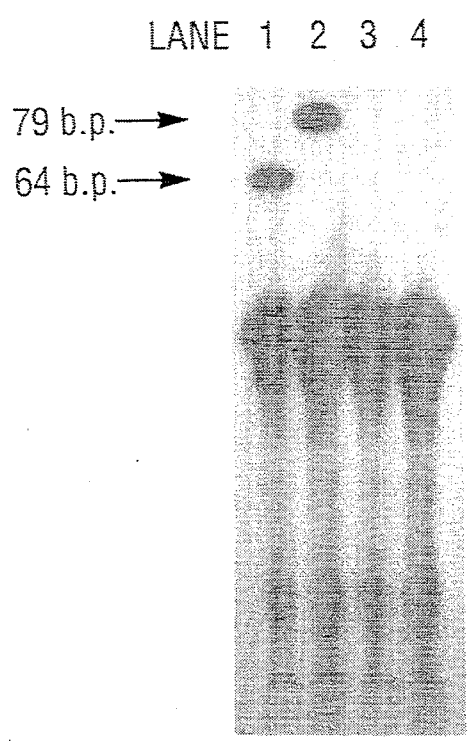
FIG. 26 is a photograph of an autoradiogram showing the quantitative destruction of ribonucleotide modified PCR-derived amplification product using RNAse A as a cutting agent, as demonstrated in Example 6.B.

A photograph of the autoradiogram is shown in FIG. 26. A comparison of the RNAse-treated and untreated modified amplification products (Reaction 1, Lane 1, and Reaction 2, Lane 2, respectively) confirms that the RNAse is cutting at the ribonucleotide site as is evident by the presence of the shorter detection product in Lane 1. Furthermore, the reaction appears to be quantitative. As expected, no detection signals are present in either of the 0 molecule controls (Lanes 3 and 4).

C. PCR Amplification of HIV in the Presence of Contamination with and without Strong Base Cutting In this experiment, wild type target molecules (plasmid pBH10) were contaminated with modified amplification product from Reaction 1K and then treated with either KOH (cutting agent) or KCl (control). After cutting to destroy the contamination, the samples were neutralized and subjected to PCR amplification to confirm that the contaminating molecules were destroyed.

Contamination was provided from reaction 1K which contained modified amplification product at a concentration of $6 \times 10^9$ molecules/$\mu$l, as quantitated in Example 6.A. This sample was serially diluted to obtain a working stock that contained 1000 molecules of modified amplification product per 5 $\mu$l. This working stock also contained HP-DNA at a concentration of 0.25 $\mu$g/$\mu$l to prevent loss of product molecules through non-specific binding.

Target DNA, HP-DNA, Reaction Buffer, dNTPs, amplification primers $AP_{18}$ and $AP_{21}'$ and labeled detection primer $PAD_5$ were the same as previously described in Example 6.A.

AmpliTaq TM DNA polymerase was obtained from Perkin-Elmer/Cetus at a concentration of 5 units/$\mu$l.

Potassium hydroxide (KOH) was dissolved in deionized water to obtain a working stock at a concentration of 600 mM.

Potassium chloride (KCl) was dissolved in deionized water to obtain a working stock at a concentration of 600 mM.

Hydrochloric acid (HCl) was diluted in deionized water to obtain a working stock at a concentration of 600 mM.

Target molecules were contaminated by mixing 5 $\mu$l of target (1000 or 0 molecules) with 5 $\mu$l of Contamination Working Stock (1000 molecules). These samples were then treated with either 5 $\mu$l of KOH or KCl working stocks (600 mM, with a final concentration of potassium of 200 mM) and heated to 94° C. for 60 minutes to complete the cutting reactions. The samples were then neutralized by adding either 5 $\mu$l of HCl to the KOH-treated samples or 5 $\mu$l of H$_2$O to the KCl-treated samples. These reactions were designated as follows:

| Reaction | KOH | KCl | HCl | H$_2$O | Target |
|---|---|---|---|---|---|
| 1 | 0 $\mu$l | 5 $\mu$l | 0 $\mu$l | 5 $\mu$l | 1000 |
| 2 | 0 $\mu$l | 5 $\mu$l | 0 $\mu$l | 5 $\mu$l | 1000 |
| 3 | 0 $\mu$l | 5 $\mu$l | 0 $\mu$l | 5 $\mu$l | 0 |
| 4 | 0 $\mu$l | 5 $\mu$l | 0 $\mu$l | 5 $\mu$l | 0 |
| 5 | 5 $\mu$l | 0 $\mu$l | 5 $\mu$l | 0 $\mu$l | 1000 |
| 6 | 5 $\mu$l | 0 $\mu$l | 5 $\mu$l | 0 $\mu$l | 1000 |
| 7 | 5 $\mu$l | 0 $\mu$l | 5 $\mu$l | 0 $\mu$l | 0 |
| 8 | 5 $\mu$l | 0 $\mu$l | 5 $\mu$l | 0 $\mu$l | 0 |

All of the reactions were then brought up to a final volume of 100 $\mu$l and were adjusted to be 1$\times$ in Reaction Buffer, and to contain each dNTP at a concentration of 100 $\mu$M, 50 picomoles of each amplification primer ($AP_{18}$ and $AP_{21}'$), and 3.2 units of AmpliTaq TM DNA polymerase. The reactions were then cycled 30 times in a Perkin-Elmer/Cetus Thermal Cycler by heating to 95° C. for 2 minutes, followed by 50° C. for 5 minutes for each cycle. The resulting amplification products were detected by combining 10 $\mu$l of each reaction with 1 $\mu$l of a solution of $^{32}$P-labeled oligonucleotide $PAD_5$ (7000 Ci/mmole, 100 femtomoles/$\mu$l) and heating to 95° C. for 2 minutes, followed by 60° C. for 10 minutes. After cooling to room temperature, 10 $\mu$l of loading buffer was added to each reaction, and the products were denatured by heating to 90° C. for 3 minutes and then cooled to room temperature. The products were analyzed by running samples on 10% denaturing PAGE, followed by autoradiography.

Figure 27:
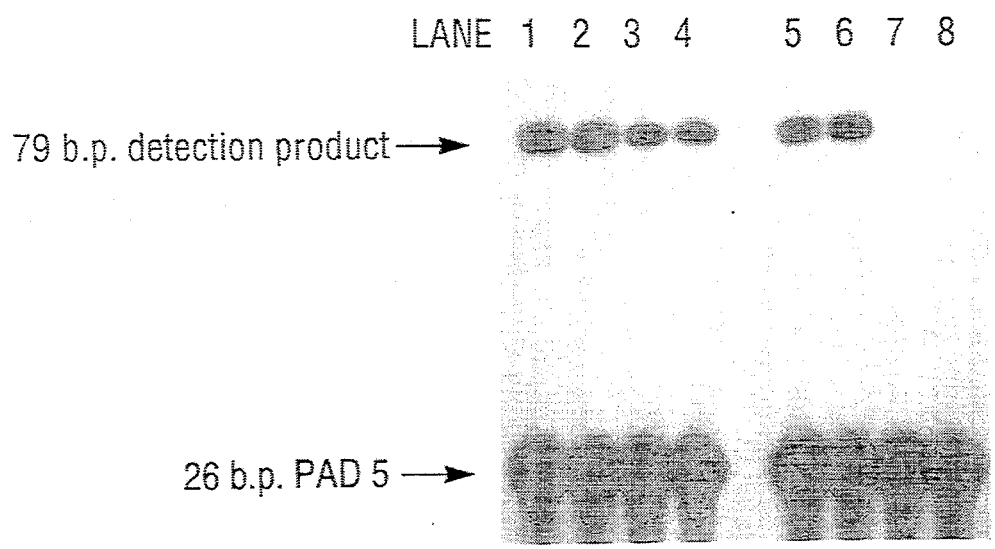
FIG. 27 is a photograph of an autoradiogram showing the effective "pre-amplification" destruction of ribonucleotide modified PCR-derived amplification product using strong base as a cutting agent, as demonstrated in Example 6.C.

A photograph of the autoradiogram is shown in FIG. 27. As expected, in the case where the samples were treated with KCl (Reactions 1-4, Lanes 1-4, respectively) the 1000 molecule target reactions cannot be distinguished from the 0 molecule target controls. This is because of the strong false positive signal resulting from the presence of 1000 molecules of contamination that remains unaffected by KCl treatment. In contrast, in the case where the samples were treated with KOH prior to amplification, the 1000 molecule target amplifications (reactions 5 and 6, Lanes 5 and 6, respectively) are easily distinguished from the corresponding 0 molecule controls (Reactions 7 and 8, Lanes 7 and 8, respectively). This is because the interfering signal from the 1000 molecules of contamination was effectively removed by the KOH treatment.

EXAMPLE 7

Ribonucleotide Modification of LCR-derived Amplification Products Chemical and Enzymatic Cleavage of Contamination In this example, several labile modifications were introduced into each strand of an amplification product produced by an LCR type of amplification. The labile bonds in this example were produced through the ligation of amplification probes that contained a single ribonucleotide on their 3'-ends. As with the similarly modified PCR-derived amplification product in Example 6, the introduction of this type of labile bond into the modified amplification product rendered it amenable to both enzymatic destruction (with RNAse A at lower temperatures) and chemical destruction (in the presence of a strong base at elevated temperatures).

A 45 base pair region of HIV was employed as the amplification sequence in this example. The 45-mer target was amplified using three pairs of amplification probes ($AP_{18}/pAP_{18}'$, $pAP_{19}/pAP_{19}$', and $pAP_{20}/pAP_{20}'$), as shown in FIG. 28.

A. LCR Amplification of HIV Using Modified Amplification Probes and Quantitative Detection of the Modified Probes In this experiment, a 45 base pair region of HIV clone, pBH10, was amplified using three pairs of amplification probes ($AP_{18}/pAP_{18}'$, $pAP_{19}/pAP_{19}'$, and $pAP_{20}/pAP_{20}'$), as shown in FIG. 28. Amplification probes $AP_{18}$, $pAP_{19}$, $pAP_{19}'$, $pAP_{20}$ and $pAP_{20}'$ contained single ribonucleotide residues on their 3'-ends, such that ligation would produce modified amplification product containing labile ribonucleotide linkages. The resulting modified amplification products were then quantitated by comparison to standards and by serial dilution, followed by re-amplification using known amounts of wild type HIV target as standards. This quantitated amplification product was then used in later experiments as controlled carryover contamination.

Thermal stable ligase (TSL) from *thermus thermophilus*, HB8 (ATCC No. 27634) and thermal stable DNA ligase buffer (TSLB) was were the same as used in Example 2.B.

Oligonucleotide $AP_{18}$ was the same as in Example 6.A. and contains a ribo-guanosine residue on its 3'-end.

Oligonucleotide $pAP_{18}'$, chemically phosphorylated on its 5'-end, was synthesized and purified as described in Example 1.

Oligonucleotides $pAP_{19}$, $pAP_{19}'$, $pAP_{20}$, and $pAP_{20}'$ were synthesized to contain both a phosphate group on their 5'-ends and a single ribonucleotide residue on their 3'-ends. The phosphate group was introduced through chemical phosphorylation, as described in example 1. The 3' ribonucleotides were introduced by initiating synthesis from the appropriate RNA supports (i.e., $pAP_{19}$ was synthesized from a RNA-G support, $pAP_{19}'$ was synthesized from a RNA-C support, $pAP_{20}$ was synthesized from a RNA-A support, and $pAP_{20}'$ was synthesized from a RNA-U support). The RNA supports were purchased from Glen Research Corporation (Herndon, Va.). After synthesis, the oligonucleotides were subjected to standard deprotection and purification protocols, as described in Example 1. It should be noted that for the following experiments, it is not necessary that $pAP_{20}$ contain a ribonucleotide on its 3'-end, nor is it necessary that oligonucleotide $pAP_{20}'$ be phosphorylated on its 5'-end. These modification were incorporated in order to make the system amenable to the use of a greater number of amplification probes in future experiments.

Amplification probe pair $AP_{18}/pAP_{18}'$ was $^{32}P$-labeled using $\gamma$-$^{32}P$-deoxyadenosine triphosphate and T4 kinase to a specific activity of approximately 7000 Ci/mmole, as described in Example 2.C. It should be noted that only amplification probe $AP_{18}$ will be labeled, because oligonucleotide $pAP_{18}'$ is already phosphorylated on its 5'-end.

HP-DNA was the same as described in Example 6.A.

Target DNA (clone pBH10) was diluted to the appropriate concentration into a solution of HP-DNA (1 $\mu g/\mu l$), and then heated in a boiling water bath for 15 minutes to fragment and denature the plasmid DNA.

All amplification reactions were run in 0.5 ml Eppendorf® tubes in a total volume of 40 $\mu l$ of 1× TSLB and contained 2 picomoles of each amplification probe ($AP_{18}$, $pAP_{18}'$, $pAP_{19}$, $pAP_{19}'$, $pAP_{20}$, and $pAP_{20}'$), an additional 100 femtomoles of $^{32}P$-labeled amplification pair $AP_{18}/pAP_{18}'$, 0.06 units of TSL, 10 $\mu g$ of HP-DNA, and were 66 $\mu M$ in NAD. Each reaction contained a total of 2.10 picomoles of amplification pair $AP_{18}/pAP_{18}'$ at an average specific activity of 333 Ci/mmole. This label provided a means to visualize the resulting amplification products. In addition to the above, the reactions also contained:

Reaction 1: 20 attomoles of target
Reaction 2: 20 attomoles of target
reaction 3: 2 attomoles of target
Reaction 4: 2 attomoles of target
Reaction 5: 0.2 attomoles of target
Reaction 6: 0.2 attomoles of target
Reaction 7: 0.0 attomoles of target
Reaction 8: 0.0 attomoles of target Two drops of mineral oil were added to each tube to prevent evaporation during amplification. The reactions were cycled 15 times in a Perkin-Elmer/Cetus Thermal Cycler by heating to 90° C. for 2 minutes, followed by 50° C. for 5 minutes for each cycle. One-eighth of each reaction (5 $\mu l$) was removed and added to 10 $\mu l$ of loading buffer. The samples were denatured by heating to 90° C. for 3 minutes, followed by cooling to room temperature. The amplification reactions were analyzed by running the samples on denaturing 15% PAGE, followed by autoradiography. Approximately 5 minutes before the electrophoretic separation was complete, known amounts of oligonucleotide pair $AP_{18}/pAP_{18}'$ (at the same specific activity used in the experiments) were loaded on the gel for use as standards in estimating the yield of amplification product. These standards appear in Lane 9 (25 femtomoles), Lane 10 (2.5 femtomoles), and Lane 11 (0.25 femtomole).

Figure 29:
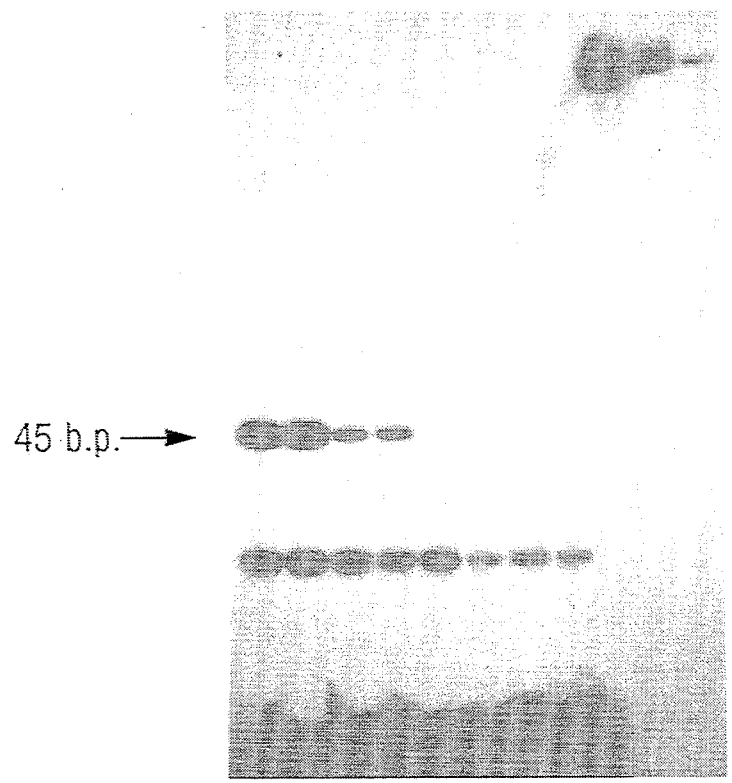
FIG. 29 is a photograph of an autoradiogram showing LCR amplification using amplification probes containing a single ribonucleotide substitution on their respective 3'-ends, as demonstrated in Example 7.A.

A photograph of the autoradiogram (FIG. 29) shows that the expected 45-mer amplification product is formed in direct response to the amount of target present at the beginning of the amplification reaction. There is not detectable signal in the zero molecule controls (reactions 7 and 8, Lane 7 and 8), while the 45 base amplification products from even the lowest target levels (0.2 attomole, Reactions 5 and 6, Lanes 5 and 6, respectively) were visible from the autoradiogram. Based on comparison of signals from the 45-mer amplification products in Reactions 1–6 (Lanes 1–6) to the standards (Lanes 9–11), the reactions are estimated to have amplified 10,000 fold. This represents an average cycle efficiency of 85%.

In order to provide a confirmation of the quantity of modified amplification product, Reaction 1 was serially diluted (based on the estimated yield of modified amplification product) and re-amplified along with wild type target standards.

All amplification reactions were run in 0.5 $\mu l$ Eppendorf® tubes in a total volume of 40 $\mu l$ of 1× TSLB, and contained 2 picomoles of each amplification probe ($AP_{18}$, $pAP_{18}'$, $pAP_{19}$, $pAP_{19}'$, $pAP_{20}$, and $pAP_{20}'$), an additional 100 femtomoles of $^{32}P$-labeled amplification probe pair $AP_{18}/pAP_{18}'$ (final specific activity of 333 Ci/mmole), and 0.06 units of TSL, 5 $\mu g$ of HP-DNA, and were 66 $\mu M$ in NAD. In addition to the above, the reactions also contained the following:

| Reaction | Target (attomoles) | Modified Amplification Product (attomoles) |
|---|---|---|
| 12 | 10 | 0 |
| 13 | 10 | 0 |
| 14 | 1 | 0 |
| 15 | 1 | 0 |
| 16 | 0 | 0 |
| 17 | 0 | 0 |
| 18 | 0 | 100 |
| 19 | 0 | 100 |
| 20 | 0 | 10 |
| 21 | 0 | 10 |
| 22 | 0 | 1 |
| 23 | 0 | 1 |

Two drops of mineral oil were added to each reaction tube to prevent evaporation during amplification. The reactions were cycled 15 times in a Perkin-Elmer/Cetus Thermal cycler by heating to 90° C. for minutes, followed by 50° C. for 5 minutes for each cycle. One-fourth of each reaction (10 $\mu l$) was removed and added to 10 $\mu l$ of loading buffer. The samples were denatured by heating to 90° C. for 3 minutes, followed by cooling to room temperature. The amplification reactions were analyzed by running the samples on denaturing 15% PAGE, followed by autoradiography.

Figure 30:
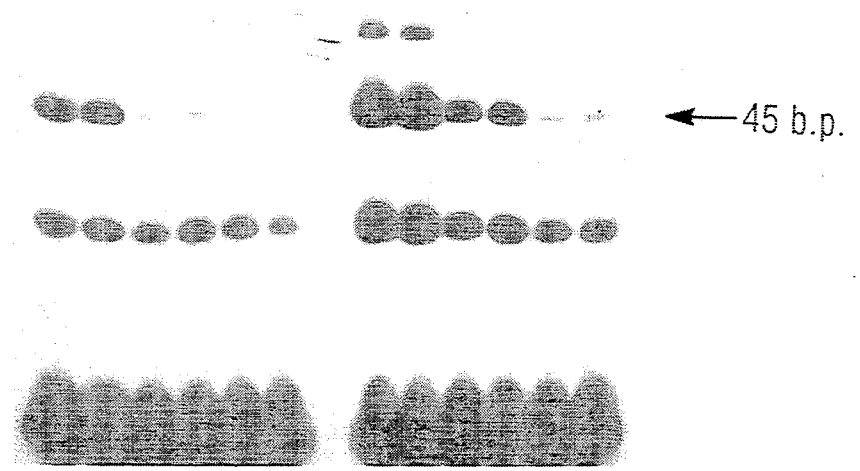
FIG. 30 is a photograph of an autoradiogram showing the quantitation of ribonucleotide modified LCR-derived amplification product by comparison to standards, as demonstrated in Example 7.A.

A photograph of the autoradiogram (FIG. 30) shows that the signals produced from the amplification of a calculated 10 attomoles of modified amplification product (Reactions 20 and 21, Lanes 20 and 21, respectively) and from 10 attomoles of wild type target (Reactions 12 and 13, Lanes 12 and 13, respectively) are equivalent. This confirms that the estimated yield of product in Reaction 1 was accurate. Modified amplification product from Reaction 1 was used in subsequent examples as contaminant amplification product.

B. LCR Amplification of HIV in the Presence of Contamination with and without Strong Base Cutting In this example, wild type target molecules (plasmid pBH10) were contaminated with modified amplification product from Reaction 1, and then treated with either KOH (cutting agent) or KCl (control). After cutting to destroy the contamination, the samples were neutralized and subjected to LCR amplification to confirm that the contaminating molecules were destroyed.

Contamination was provided to the reaction mixtures in the form of modified amplification product from Reaction 1 (as quantitated in Example 7.A) to be at a level of 5 femtomoles of product per 1 μl of reaction mixture. This product was diluted and added to the reaction mixtures at the desired concentration.

Potassium Hydroxide (KOH) was dissolved in deionized water to obtain a working stock at a concentration of 700 mM.

Potassium Chloride (KCl) was dissolved in deionized water to obtain a working stock at a concentration of 700 mM.

Hydrochloric Acid (HCl) was dissolved in deionized water to obtain a working stock at a concentration of 700 mM.

All other reagents were the same as in Example 7.A.

Reactions containing target (10 attomoles or 0 attomoles), Contamination (10 attomoles), HP-DNA (5 μg) and amplification probes (2.0 picomoles each of $AP_{18}/pAP_{18}'$, $pAP_{19}/pAP_{19}'$, and $pAP_{20}/pAP_{20}'$, and 0.10 picomole of $^{32}$P-labeled $AP_{18}/pAP_{18}'$) in a volume of 18 μl were then treated with either 4 μl KOH or KCl working stocks (700 mM, with a final reaction concentration of 127 mM) and heated to 90° C. for 30 minutes to complete the cutting reaction. The reactions were then neutralized with 4 μl of HCl or H$_2$O, and subjected to LCR amplification as described below. The reactions were designated as follows:

| Reaction | KOH | KCl | HCl | H$_2$O | Target (amoles) |
|---|---|---|---|---|---|
| 1 | 4 μl | 0 μl | 4 μl | 0 μl | 10 |
| 2 | 4 μl | 0 μl | 4 μl | 0 μl | 10 |
| 3 | 4 μl | 0 μl | 4 μl | 0 μl | 0 |
| 4 | 4 μl | 0 μl | 4 μl | 0 μl | 0 |
| 5 | 0 μl | 4 μl | 0 μl | 4 μl | 10 |
| 6 | 0 μl | 4 μl | 0 μl | 4 μl | 10 |
| 7 | 0 μl | 4 μl | 0 μl | 4 μl | 0 |
| 8 | 0 μl | 4 μl | 0 μl | 4 μl | 0 |

All of the reactions were then brought up to a final volume of 40 μl, so that they were 1× in TSLB, 66 μM in NAD, and contained 0.06 units of TSL. Two drops of mineral oil were added to each reaction to prevent evaporation using amplification. The reactions were then cycled 15 times in a Perkin-Elmer/Cetus Thermal Cycler by heating to 90° C. for 2 minutes, followed by 50° C. for 5 minutes for each cycle. One-eighth of the reactions (5 μl) was removed and added to 10 μl of loading buffer, and denatured by heating to 90° C. for 3 minutes. The resulting products were analyzed by running the samples on denaturing 15% PAGE, followed by autoradiography.

Figure 31:
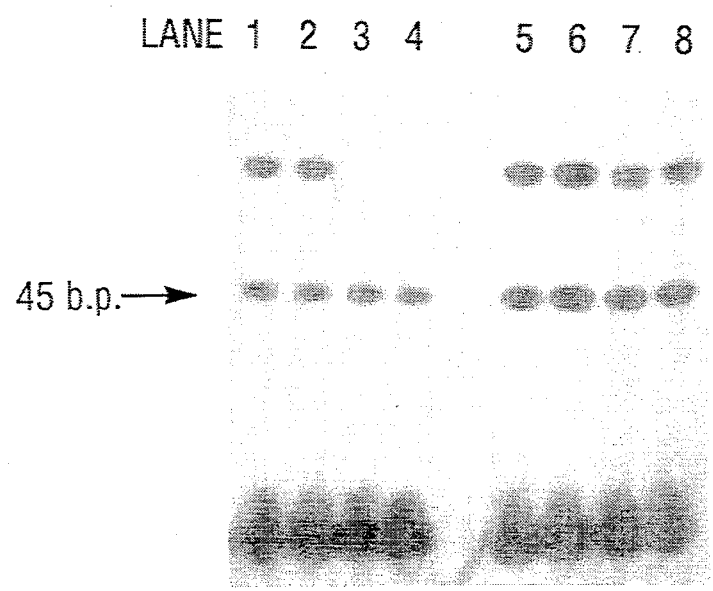
FIG. 31 is a photograph of an autoradiogram showing the effective "pre-amplification" destruction of ribonucleotide modified LCR-derived amplification product using strong base as a cutting agent, as demonstrated in Example 7.B.

A photograph of the autoradiogram (FIG. 31) shows that the contaminated samples treated with KCl gave 10 attomole target signals (Reactions 5 and 6, Lanes 5 and 6, respectively) that are indistinguishable from the zero attomole target signals (Reactions 7 and 8, Lanes 7 and 8, respectively). This is expected, due to the interfering signal resulting from the 10 attomoles of contamination. In contrast, the samples that were treated with KOH show no signal from the zero attomole target reactions (Reactions 3 and 4, Lanes 3 and 4, respectively) and the 10 attomole target signals (Reactions 1 and 2, Lanes 1 and 2, respectively) are clearly positive above the zeroes. This demonstrates that the KOH cutting agent effectively eliminates any interfering signals due to the presence of contamination.

C. LCR Amplification of HIV Followed by Cutting with RNAse A

In this example, a portion of HIV was amplified using the same modified amplification probes (FIG. 28) used in the previous examples, with the resulting products being subjected to RNAse A as a cutting agent. Because RNAse A is specific for pyrimidine residues, the treatment should cut only the lower strand of the amplification product. The lower strand of the resulting modified amplification product contains two internal ribopyrimidine linkages, while the upper strand contains two internal ribo-purine residues. For this reason, amplification probe $pAP_{20}'$ was labeled with $^{32}$P such that only the lower strand of the resulting amplification product was labeled.

Because $pAP_{20}'$ already contains a 5'-phosphate group, the $^{32}$P-label was introduced by an exchange kination procedure by the following procedure. Ten units of T4 polynucleotide kinase (New England Biolabs, Inc.) was added to a solution containing 1.0 picomole of oligonucleotide $pAP_{20}'$, 2.5 nanomoles of adenosine 5'-phosphate (ADP, Sigma Chemical Company), and 100 picomoles of γ-$^{32}$P-adenosine 5'-triphosphate (ATP, 7000 Ci/mmole) in 10 μl of buffer (40 mM tris, pH 7.6/10 mM MGCl$_2$/12.5 mM DTT). The reaction mixture was allowed to incubate at 37° C. for 30 minutes, followed by 90° C. for 5 minutes, to stop the exchange reaction. The labeled oligonucleotide was then separated from excess label by passing the reaction through a Sephadex ®G-50 column (Sigma Chemical Company) using 10 mM triethyl ammonium bicarbonate as an eluent. The fractions containing the oligonucleotide were combined and evaporated using a Speed-Vac ® concentrator (Savant Instruments, Inc., Farmingdale, N.Y.). The product was re-suspended in 20 μl of TE (50 femtomoles/μl) and determined to have a specific activity of approximately 3500 Ci/mmole.

Amplification probes ($AP_{18}/pAP_{18}'$, $pAP_{19}/pAP_{19}'$, and $pAP_{20}/pAP_{20}'$), thermal stable ligase (TSL), thermal stable DNA ligase buffer (TSLB), carrier DNA (HP-DNA, and target DNA (plasmid pBH10) were the same as describe in Example 7.A.

RNAse A (Sigma Chemical Company) was dissolved in TE/150 mM NaCl at a concentration of 10 mg/ml. Contaminating DNAse activity was destroyed by heating this solution for 15 minutes in a boiling water bath. A 1/20 dilution of this stock in TE was used in the following experiment.

All amplification reactions were run in 0.5 ml Eppendorf ® tubes in a total volume of 20 μl of 1× TSLB and contained 1.0 picomoles of each amplification probe ($AP_{18}$, $pAP_{18}'$, $pAP_{19}$, $pAP_{19}'$, $pAP_{20}$, and $pAP_{20}'$), and an additional 50 femtomoles of $^{32}$P-labeled amplification probe $pAP_{20}'$, 0.03 units of TSL, 5 μg of HP-DNA, and were 66 mM in NAD. Each reaction thus contained a total of 1.05 picomoles of $pAP_{20}'$ at a final specific activity of approximately 167 Ci/mmole. This label was provided as a means to visualize the lower strand of the resulting amplification products. In addition to the above, the reactions also contained:
Reaction 1: 0.0 attomoles of target
Reaction 2: 0.0 attomoles of target
Reaction 3: 10.0 attomoles of target
Reaction 4: 10.0 attomoles of target Two drops of mineral oil were added to each tube to prevent evaporation during amplification. The reactions were cycled 15 times in a Perkin-Elmer/Cetus Thermal Cycler by heating to 90° C. for 2 minutes, followed by 50° C. for 5 minutes for each cycle. One-fourth (5 μl) of the reactions were added to 5 μl of loading buffer, and then denatured by heating to 90° C. for 3 minutes and cooling to room temperature. An additional one-fourth (5 μl) of each of the reactions was removed and treated with 2 μl of RNAse A solution (1.0 μg). Each of the reactions was incubated at room temperature for 60 minutes and subsequently quenched by the addition of 5 μl of loading buffer to each sample, followed by heating to 90° C. for 3 minutes, and then cooling to room temperature. Reactions treated with RNAse A were designated Reactions 1R, 2R, 3R, and 4R.

Figure 32:
FIG. 32 is a photograph of an autoradiogram showing the quantitative destruction of ribonucleotide modified LCR-derived amplification product using RNAse A as a cutting agent, as demonstrated in Example 7.C.

The reaction products were analyzed by running the samples on denaturing 10% PAGE followed by autoradiography. A photograph of the autoradiogram (FIG. 32) shows the expected 45-mer amplification product in the 10 attomole target reactions (Reactions 3 and 4, Lanes 3 and 4, respectively), while the corresponding zero target controls (Reactions 1 and 2, Lanes 1 and 2, respectively) show no sign of amplification product. In contrast, none of the samples treated with RNAse A show any sign of 45-mer amplification product (Reactions 1R, 2R, 3R, and 4R, Lanes 5, 6, 7, and 8, respectively). This confirms that the modified amplification product is effectively destroyed by the RNAse A cutting agent.

What is claimed is:

1. A method for reducing DNA carryover contamination in a first test sample which may contain amplification product from a previously amplified DNA target-containing test sample comprising:
   (a) amplifying said DNA target of said previous test sample in the presence of at least one modified amplification probe or primer to generate a modified amplification product having an enzyme recognition site or chemically cleavable site not present in said target; and,
   (b) contacting said first test sample with a means for cleaving said modified amplification product to reduce the amount of modified amplification product from said previous test sample thereby reducing DNA carryover contamination present in said first test sample.

2. The method of claim 1 wherein said modified amplification product has is an enzyme recognition site and said means for cleaving said modified amplification product is an enzyme.

3. The method of claim 2 wherein said enzyme recognition site is an RNAse recognition site and said means for cleaving said modified amplification product is an RNAse.

4. The method of claim 3 wherein said RNAse is selected from the group consisting of RNAse H and RNAse A.

5. The method of claim 4 wherein said RNAse is RNAse A.

6. The method of claim 2 wherein said enzyme recognition site is a restriction enzyme recognition site and said means for cleaving said modified amplification product is a restriction enzyme.

7. The method of claim 6 wherein said restriction enzyme recognition site is recognized by a remote cutting restriction enzyme.

8. The method of claim 7 wherein said remote cutting restriction enzyme is Fok I.

9. The method of claim 1 wherein said modified amplification product has a chemically cleavable site.

10. The method of claim 9 wherein said chemically cleavable site is incorporated into an amplification probe by joining the 3'- and 5'-ends of partial probe sequences with a homobifunctional linking reagent selected from the group consisting of dithiobis(succinimidyl-propionate), disuccinimidyl-tartarate, and ethylene glycolbis (succinimidylsuccinate).

11. The method of claim 9 wherein said chemically cleavable site comprises an RNA base substitution.

12. A kit for reducing DNA carryover contamination in a polymerase chain reaction type of amplification procedure comprising:
   (a) at least one modified amplification primer which is capable of incorporating at least one modification into a PCR-derived amplification product such that the resulting modified PCR-derived amplification product has a remote cutting restriction enzyme recognition site not present in said target sequence; and,
   (b) a remote cutting restriction enzyme.

13. The kit of claim 12 wherein said remote cutting restriction enzyme is Fok I.

14. A kit for reducing DNA carryover contamination in a ligase chain reaction type of amplification procedure comprising:
   (a) at least one upper strand and at least one lower strand modified amplification probe which are capable of incorporating at least one upper strand and at least one lower strand modification into a remote cutting restriction LCR-derived amplification product such that the resulting modified LCR-derived amplification product has an enzyme recognition site not present in said target sequence; and,
   (b) a remote cutting restriction enzyme.

15. The kit of claim 14 wherein said remote cutting restriction enzyme is Fok I.

16. A method for reducing DNA carryover contamination in a method for amplifying a target sequence comprising the steps of:
   (a) hybridizing at least two amplification primers to said target sequence in the presence of an excess of deoxynuclcoside triphosphates and a polymerizing agent, wherein at least one of said amplification primers is a modified amplification primer having a modification selected from the group consisting of an enzyme recognition site and a chemically cleavable site;
   (b) extending said amplification primers with said deoxynucleoside triphosphates and said polymerizing agent to generate amplification product such that modified amplification product is generated from extension of each modified amplification primer;
   (c) separating said modified amplification product from said target sequence;
   (d) repeating steps (a) through (c); and (e) cleaving said modified amplification product thereby reducing DNA carryover contamination in a method for amplifying a target sequence.

17. The method of claim 16 wherein step (e) is performed at an beginning of the amplification procedure.

18. The method of claim 16 further comprising:
(f) detecting the amount of cleaved modified amplification product after performing g step (e).

19. A method for reducing DNA carryover contamination in a method for amplifying a denatured double-stranded target sequence comprising the steps of:
(a) contiguously hybridizing at least two pairs of amplification probes to said denatured double stranded target sequence, wherein at least one upper strand and at least one lower strand of said pairs of amplification probes is a modified amplification probe having a modification selected from the group consisting of an enzyme recognition site and a chemically clearable site;
(b) ligating said contiguously hybridized amplification probes to generate modified amplification product thereby reducing DNA carryover contamination in a method for amplifying a denatured double stranded target sequence;
(c) separating said modified amplification product from said target sequence;
(d) repeating steps (a) through (c);
(e) cleaving said modified amplification product.

20. The method of claim 19 wherein step (e) is performed at a beginning of the amplification procedure.

21. The method of claim 19 further comprising:
(f) detecting the amount of cleaved modified amplification product after performing step (e).

* * * * *

Adverse Decision In Interference

Patent No. 5,427,929, Rodney M. Richards, Theodore Jones, David L. Snitman, Gregory S. Brown, METHOD FOR REDUCING CARRYOVER CONTAMINATION IN AN AMPLIFICATION PROCEDURE, Interference No. 105,257, final judgment adverse to the patentees rendered June 10, 2005, as to claims 1, 2 and 19-21.

(*Official Gazette, November 22, 2005*)